(12) United States Patent
Wolschek et al.

(10) Patent No.: US 9,187,732 B2
(45) Date of Patent: Nov. 17, 2015

(54) REPLICATION DEFICIENT INFLUENZA VIRUS FOR THE EXPRESSION OF HETEROLOGOUS SEQUENCES

(71) Applicant: Baxter Healthcare SA, Glattpark (Opfikon) (CH)

(72) Inventors: Markus Wolschek, Vienna (AT); Andrej Egorov, Vienna (AT); Michael Bergmann, Klosterneuburg (AT); Thomas Muster, Vienna (AT); Christian Kittel, Vienna (AT)

(73) Assignee: Baxalta GmbH, Opfikon (CH)

( * ) Notice: Subject to any disclaimer, the term of this patent is extended or adjusted under 35 U.S.C. 154(b) by 0 days.

(21) Appl. No.: 14/049,601

(22) Filed: Oct. 9, 2013

(65) Prior Publication Data

US 2014/0045245 A1   Feb. 13, 2014

Related U.S. Application Data

(63) Continuation of application No. 12/666,246, filed as application No. PCT/EP2008/058154 on Jun. 26, 2008, now abandoned.

(60) Provisional application No. 60/946,644, filed on Jun. 27, 2007.

(30) Foreign Application Priority Data

Oct. 5, 2007   (EP) .................................... 07450176

(51) Int. Cl.
*A61K 39/00*   (2006.01)
*C07K 14/005*   (2006.01)
*C12N 7/00*   (2006.01)
*C12N 15/86*   (2006.01)

(52) U.S. Cl.
CPC ................ *C12N 7/00* (2013.01); *C07K 14/005* (2013.01); *C12N 15/86* (2013.01); *A61K 39/00* (2013.01); *A61K 2039/525* (2013.01);
(Continued)

(58) Field of Classification Search
CPC ............. C07K 2317/92; C07K 14/005; A61K 2039/525
USPC ........................................................ 435/236
See application file for complete search history.

(56) References Cited

FOREIGN PATENT DOCUMENTS

WO   WO99/64068   12/1999
WO   WO99/64571   12/1999
(Continued)

OTHER PUBLICATIONS

Kittel et al., Rescue of influenza virus expressing GFP from the NS1 reading frame, 2004, Virology, 324:67-73.*
(Continued)

*Primary Examiner* — Zachariah Lucas
*Assistant Examiner* — Barry A Chestnut
(74) *Attorney, Agent, or Firm* — Michael Fedrick; Loza & Loza, LLP

(57) ABSTRACT

The present invention relates to a novel replication deficient influenza virus comprising a modified NS1 segment coding for a NS1 protein lacking a functional RNA binding domain and functional effector domain and having a heterologous sequence inserted between the splice donor site and the splice acceptor site of the NS gene segment. The virus can be used as vector for expression of various proteins like chemokines, cytokines or antigenic structures and to produce vaccines. A fusion peptide comprising part of the N-terminus of an NS1 protein and a signal sequence fused to the C-terminus of said NS1 peptide is also provided.

19 Claims, 22 Drawing Sheets

Figure 2:
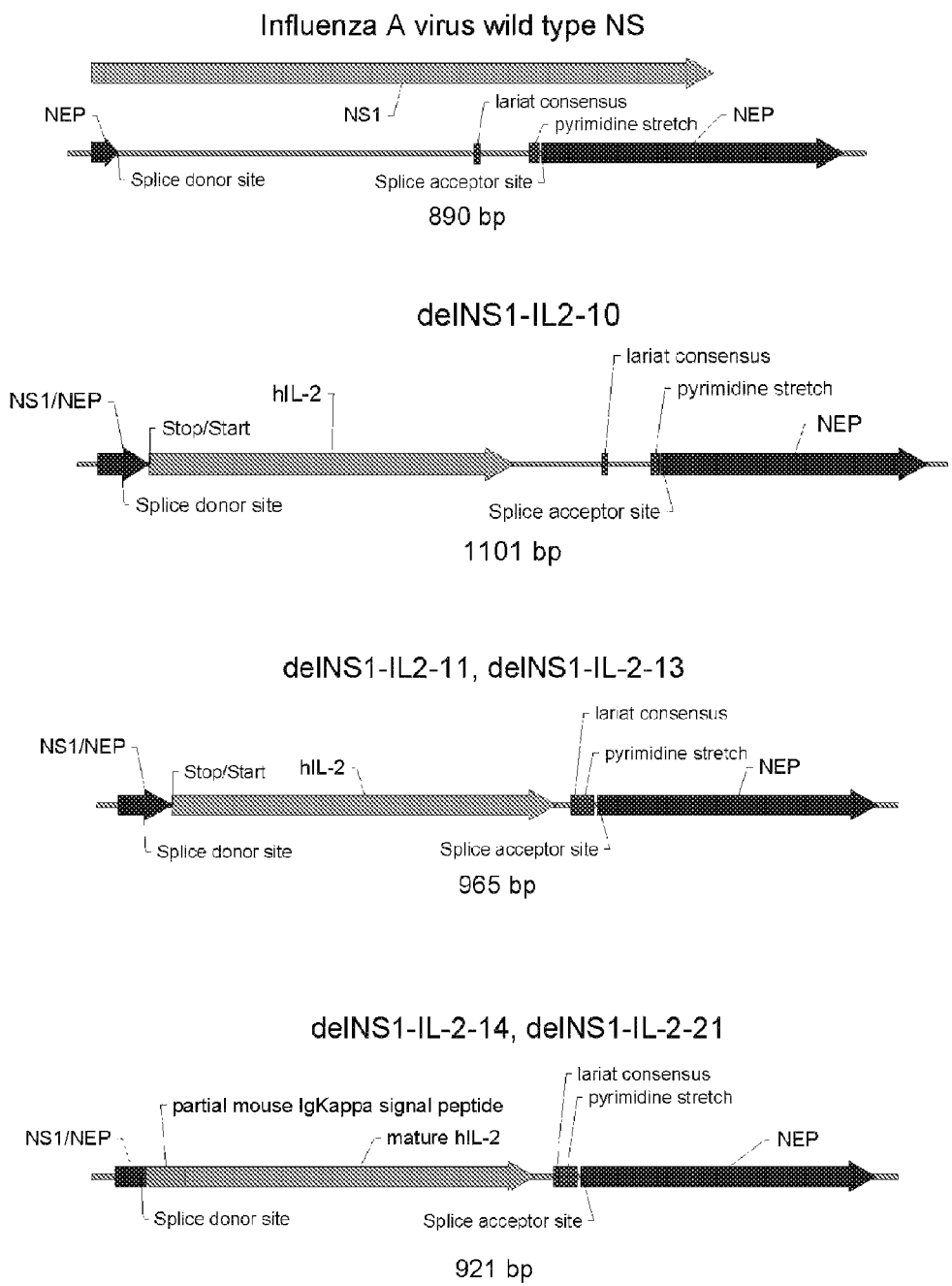

(52) U.S. Cl.
CPC ............... *A61K 2039/5256* (2013.01); *C12N 2760/16132* (2013.01); *C12N 2760/16143* (2013.01); *C12N 2760/16243* (2013.01)

(56) References Cited

FOREIGN PATENT DOCUMENTS

| WO | WO01/64860 | * | 7/2001 |
|---|---|---|---|
| WO | WO01/64860 | | 9/2001 |
| WO | WO2004/108760 | | 12/2004 |
| WO | WO2006/088481 | | 8/2006 |
| WO | WO2006/119527 | | 11/2006 |
| WO | WO2007/016715 | * | 2/2007 |

OTHER PUBLICATIONS

Kittel et al. Generation of an Influenza A Virus Vector Expressing Biologically Active Human Interleukin-2 from the NS Gene Segment, Aug. 2005, Journal of Virology, (79)16: pp. 10672-10677.*
Tang et al. Vector Prime/Protein Boost Vaccine that overcomes defects acquired during aging and cancer, Jul. 2006, The Journal of Immunology, 177:5697-5707.*
Garcia et al., Influenza A Virus Lacking the NS1 Gene Replicates in Interferon-Deficient Systems, 1998, 252:324-330.*
Kittel C. et al. "Rescue of influenza virus expressing GFP from the NS1 reading frame" Virology 324:67-73, 2004.
Office Action, European Patent Application No. 08774337.3, Oct. 20, 2010.
International Search Report, International Patent Application No. PCT/EP2008/058154, Mar. 17, 2009.
International Written Opinion, International Patent Application No. PCT/EP2008/058154, Mar. 17, 2009.
International Preliminary Report on Patentability, International Patent Application No. PCT/EP2008/058154, Jan. 5, 2010.
Aqueilan R, et al, Biochem. J, 2003, No. 370, pp. 129-140.
Bergmann M, et al, Cancer Research, 2001, vol. 61, No. 22, pp. 8188-8193.
Caton A J, et al, Cell, 1982, vol. 31, pp. 417-427.
Enami M, et al, Journal of Virology, 2000, vol. 74, No. 12, pp. 5556-5561.
Ferko B, et al, Journal of Virology, 2001, vol. 75, No. 19, pp. 8899-8908.
Ferko B, et al, Journal of Virology, 2004, vol. 78, No. 23, pp. 13037-13045.
Ferko B, et al, Journal of Virology, 2006, vol. 80, No. 23, pp. 11621-11627.
Flick R, et al, Virology, 1999, vol. 262, pp. 93-103.
Garcia-Sastre A, et al, Journal of Virology, 1994, vol. 68, No. 10, pp. 6254-6261.
Herlocher M L, et al, PNAS, 1993, vol. 90, pp. 6032-6036.
Herlocher M L, et al, Virus Research, 1996, vol. 42, pp. 11-25.
Hoffmann E, et al, PNAS, 2000, vol. 97, No. 11, pp. 6108-6113.
Kozak M, Nucleic Acids Research, 1984, vol. 12, No. 2, pp. 857-872.
Kozak M, Nucleic Acids Research, 1987, vol. 15, No. 20, pp. 8125-8148.
Machado A V, et al, Virology, 2003, vol. 313, pp. 235-249.
Muster T, et al, Journal of Virology, 1994, vol. 68, No. 6, pp. 4031-4034.
Nemeroff M E, et al, Mol Cell Biol, 1992, vol. 12, No. 3, ppa 962-970.
Neumann G, et al, Adv Virus Res, 1999, vol. 53, pp. 265-300.
Perca N, et al, Journal of Virology, 1994, vol. 68, No. 7, pp. 4486-4492.
Pleschka S, et al, Journal of Virology, 1996, vol. 70, No. 6, pp. 4188-4192.
Plotch S J, et al, PNAS, 1986, vol. 83, pp. 5444-5448.
Schultz-Cherry S, et al, Journal of Virology, 2001, vol. 75, No. 17, pp. 7875-7881.
Stukova M A, et al, Tuberculosis, 2006, vol. 86, No. 3-4, pp. 236-246.
Takasuka N, et al, Vaccine, 2002, vol. 20, No. 11-12, pp. 1579-1585.
Treanor J, et al, Journal of Virology, 1994, vol. 68, No. 17, pp. 7684-7688.
Wang W, et al, Virology, 1996, vol. 223, pp. 41-50.
Watanabe T, et al, Journal of Virology, vol. 77, No. 19, pp. 10575-10583.
Yoneyama M, et al, Nat Immunol, 2004, vol. 5, No. 7, pp. 730-737.

* cited by examiner

```
AGCAAAAGCAGGGTGACAAAAACATAATGGATCCAAACACTGTGTCAAGC          50
TTTCAGGTAAGTATCTTTCTTTGGCGTGTCCGCAAACGATAATGTACAGG         100
ATGCAACTCCTGTCTTGCATTGCACTAAGTCTTGCACTTGTCACAAACAG         150
TGCACCTACTTCTTCGTCGACAAAGAAAACACAGCTACAACTGGAGCATT         200
TACTGCTGGATTTACAGATGATTTTGAATGGAATTAATAATTACAAGAAT         250
CCCAAACTCACCAGGATGCTCACATTTAAGTTTTACATGCCCAAGAAGGC         300
CACAGAACTGAAACATCTTCAGTGTCTAGAAGAAGAACTCAAACCTCTGG         350
AGGAAGTGCTAAATTTAGCTCAAAGCAAAAACTTTCACTTAAGACCCAGG         400
GACTTAATCAGCAATATCAACGTAATAGTTCTGGAACTAAAGGGATCTGA         450
AACAACATTCATGTGTGAATATGCTGATGAGACAGCAACCATTGTAGAAT         500
TTCTGAACAGATGGATTACCTTTTGTCAAAGCATCATCTCAACACTAACT         550
TGATAACCAAGCAGAAAGTGGCAGGCCCTCTTTGTATCAGAATGGACCAG         600
GCGATCATGGATAAGAACATCATACTGAAAGCGAACTTCAGTGTGATTTT         650
TGACCGGCTGGAGACTCTAATATTGCTAAGGGCTTTCACCGAAGAGGGAG         700
CAATTGTTGGCGAAATTTCACCATTGCCTTCTCTTCCAGGACATACTGCT         750
GAGGATGTCAAAAATGCAGTTGGAGTCCTCATCGGGGGACTTGAATGGAA         800
TGATAACACAGTTCGAGTCTCTGAAACTCTACAGAGATTCGCTTGGAGAA         850
GCAGTAATGAGAATGGGAGACCTCCACTCACTCCAAAACAGAAACGAGAA         900
ATGGCGGGAACAATTAGGTCAGAAGTTTGAAGAAATAAGATGGTTGATTG         950
AAGAAGTGAGACACAAACTGAAGATAACAGAGAATAGTTTTGAGCAAATA        1000
ACATTTATGCAAGCCTTACATCTATTGCTTGAAGTGGAGCAAGAGATAAG        1050
AACTTTCTCGTTTCAGCTTATTTAATAATAAAAAACACCCTTGTTTCTAC        1100
T                                                         1101
```

Figure 1a

```
AGCAAAAGCAGGGTGACAAAAACATAATGGATCCAAACACTGTGTCAAGC      50
TTTCAGGTAAGTATCTTTCTTTGGCGTGTCCGCAAACGATAATGTACAGG     100
ATGCAACTCCTGTCTTGCATTGCACTAAGTCTTGCACTTGTCACAAACAG     150
TGCACCTACTTCTTCGTCGACAAAGAAAACACAGCTACAACTGGAGCATT     200
TACTGCTGGATTTACAGATGATTTTGAATGGAATAATAATTACAAGAAT      250
CCCAAACTCACCAGGATGCTCACATTTAAGTTTTACATGCCCAAGAAGGC     300
CACAGAACTGAAACATCTTCAGTGTCTAGAAGAAGAACTCAAACCTCTGG     350
AGGAAGTGCTAAATTTAGCTCAAAGCAAAAACTTTCACTTAAGACCCAGG    400
GACTTAATCAGCAATATCAACGTAATAGTTCTGGAACTAAAGGGATCTGA    450
AACAACATTCATGTGTGAATATGCTGATGAGACAGCAACCATTGTAGAAT    500
TTCTGAACAGATGGATTACCTTTTGTCAAAGCATCATCTCAACACTAACT    550
TGATAACCAAGCAGAAAGTGGTACTAACCTTCTTCTCTTTCTTCTCCTGA    600
CAGGACATACTGCTGAGGATGTCAAAAATGCAGTTGGAGTCCTCATCGGG    650
GGACTTGAATGGAATGATAACACAGTTCGAGTCTCTGAAACTCTACAGAG    700
ATTCGCTTGGAGAAGCAGTAATGAGAATGGGAGACCTCCACTCACTCCAA    750
AACAGAAACGAGAAATGGCGGGAACAATTAGGTCAGAAGTTTGAAGAAAT    800
AAGATGGTTGATTGAAGAAGTGAGACACAAACTGAAGATAACAGAGAATA    850
GTTTTGAGCAAATAACATTTATGCAAGCCTTACATCTATTGCTTGAAGTG    900
GAGCAAGAGATAAGAACTTTCTCGTTTCAGCTTATTTAATAATAAAAAAC    950
ACCCTTGTTTCTACT                                       965
```

Figure 1b

```
AGCAAAAGCAGGGTGACAAAAACATAATGGATCCAAACACTGTGTCAAGC      50
TTTCAGGTAAGTCTCCTGCTTTGGGTACTGCTGCTCTGGGTTCCAGGTTC     100
CACTGGTGCACCTACTTCTTCGTCGACAAAGAAAACACAGCTACAACTGG     150
AGCATTTACTGCTGGATTTACAGATGATTTTGAATGGAATTAATAATTAC     200
AAGAATCCCAAACTCACCAGGATGCTCACATTTAAGTTTTACATGCCCAA     250
GAAGGCCACAGAACTGAAACATCTTCAGTGTCTAGAAGAAGAACTCAAAC     300
CTCTGGAGGAAGTGCTAAATTTAGCTCAAAGCAAAAACTTTCACTTAAGA     350
CCCAGGGACTTAATCAGCAATATCAACGTAATAGTTCTGGAACTAAAGGG     400
ATCTGAAACAACATTCATGTGTGAATATGCTGATGAGACAGCAACCATTG     450
TAGAATTTCTGAACAGATGGATTACCTTTTGTCAAAGCATCATCTCAACA     500
CTAACTTGATAACCAAGCAGAAAGTGGTACTAACCTTCTTCTCTTTCTTC     550
TCCTGACAGGACATACTGCTGAGGATGTCAAAAATGCAGTTGGAGTCCTC     600
ATCGGGGACTTGAATGGAATGATAACACAGTTCGAGTCTCTGAAACTCT      650
ACAGAGATTCGCTTGGAGAAGCAGTAATGAGAATGGGAGACCTCCACTCA     700
CTCCAAAACAGAAACGAGAAATGGCGGGAACAATTAGGTCAGAAGTTTCA     750
AGAAATAAGATGGTTGATTGAAGAAGTGAGACACAAACTGAAGATAACAG     800
AGAATAGTTTTGAGCAAATAACATTTATGCAAGCCTTACATCTATTGCTT     850
GAAGTGGAGCAAGAGATAAGAACTTTCTCGTTTCAGCTTATTTAATAATA     900
AAAAACACCCTTGTTTCTACT                                 921
```

Figure 1c

```
AGCAAAAGCAGGGTGACAAAAACATAATGGATCCAAACACTGTGTCAAGC         50
TTTCAGGTAGATTGCTTTCTTTGGCGTGTCCGCAAACGATAATGTACAGG        100
ATGCAACTCCTGTCTTGCATTGCACTAAGTCTTGCACTTGTCACAAACAG        150
TGCACCTACTTCTTCGTCGACAAAGAAAACACAGCTACAACTGGAGCATT        200
TACTGCTGGATTTACAGATGATTTGAATGGAATTAATAATTACAAGAAT         250
CCCAAACTCACCAGGATGCTCACATTTAAGTTTTACATGCCCAAGAAGGC        300
CACAGAACTGAAACATCTTCAGTGTCTAGAAGAAGAACTCAAACCTCTGG        350
AGGAAGTGCTAAATTTAGCTCAAAGCAAAAACTTTCACTTAAGACCCAGG        400
GACTTAATCAGCAATATCAACGTAATAGTTCTGGAACTAAAGGGATCTGA        450
AACAACATTCATGTGTGAATATGCTGATGAGACAGCAACCATTGTAGAAT        500
TTCTGAACAGATGGATTACCTTTTGTCAAAGCATCATCTCAACACTAACT        550
TGATAACCAAGCAGAAAGTGGTACTAACCTTCTTCTCTTTCTTCTCCTGA        600
CAGGACATACTGCTGAGGATGTCAAAAATGCAGTTGGAGTCCTCATCGGG        650
GGACTTGAATGGAATGATAACACAGTTCGAGTCTCTGAAACTCTACAGAG        700
ATTCGCTTGGAGAAGCAGTAATGAGAATGGGAGACCTCCACTCACTCCAA        750
AACAGAAACGAGAAATGGCGGGAACAATTAGGTCAGAAGTTTGAAGAAAT        800
AAGATGGTTGATTGAAGAAGTGAGACACAAACTGAAGATAACAGAGAATA        850
GTTTGAGCAAATAACATTTATGCAAGCCTTACATCTATTGCTTGAAGTG        900
GAGCAAGAGATAAGAACTTTCTCGTTTCAGCTTATTTAGTACTAAAAAAC        950
ACCCTTGTTTCTACT                                          965
```

Figure 1d

```
AGCAAAAGCAGGGTGACAAAAACATAATGGATCCAAACACTGTGTCAAGC         50
TTTCAGGTATTTGCCCTGCTTTGGGTACTGCTGCTCTGGGTTCCAGGTTC        100
CACTGGTGCACCTACTTCTTCGTCGACAAAGAAAACACAGCTACAACTGG        150
AGCATTTACTGCTGGATTTACAGATGATTTTGAATGGAATTAATAATTAC        200
AAGAATCCCAAACTCACCAGGATGCTCACATTTAAGTTTTACATGCCCAA        250
GAAGGCCACAGAACTGAAACATCTTCAGTGTCTAGAAGAAGAACTCAAAC        300
CTCTGGAGGAAGTGCTAAATTTAGCTCAAAGCAAAAACTTTCACTTAAGA        350
CCCAGGGACTTAATCAGCAATATCAACGTAATAGTTCTGGAACTAAAGGG        400
ATCTGAAACAACATTCATGTGTGAATATGCTGATGAGACAGCAACCATTG        450
TAGAATTTCTGAACAGATGGATTACCTTTTGTCAAAGCATCATCTCAACA        500
CTAACTTGATAACCAAGCAGAAAGTGGTACTAACCTTCTTCTCTTTCTTC        550
TCCTGACAGGACATACTGCTGAGGATGTCAAAAATGCAGTTGGAGTCCTC        600
ATCGGGGGACTTGAATGGAATGATAACACAGTTCGAGTCTCTGAAACTCT        650
ACAGAGATTCGCTTGGAGAAGCAGTAATGAGAATGGGAGACCTCCACTCA        700
CTCCAAAACAGAAACGAGAAATGGCGGGAACAATTAGGTCAGAAGTTTGA        750
AGAAATAAGATGGTTGATTGAAGAAGTGAGACACAAACTGAAGATAACAG        800
AGAATAGTTTTGAGCAAATAACATTTATGCAAGCCTTACATCTATTGCTT        850
GAAGTGGAGCAAGAGATAAGAACTTTCTCGTTTCAGCTTATTTAATAATA        900
AAAAACACCCTTGTTTCTACT                                     921
```

Figure 1e

```
AGCAAAAGCAGGGTGACAAAAACATAATGGATCCAAACACTGTGTCAAGC        50
TTTCAGGTAAGTATCTTTCTTTGGCGTGTCCGCAAACGATAAGCCGCCAC       100
CATGTACAGGATGCAACTCCTGTCTTGCATTGCACTAAGTCTTGCACTTG       150
TCACAAACAGTGCACCTACTTCTTCGTCGACAAAGAAAACACAGCTACAA       200
CTGGAGCATTTACTGCTGGATTTACAGATGATTTGAATGGAATTAATAA       250
TTACAAGAATCCCAAACTCACCAGGATGCTCACATTTAAGTTTTACATGC       300
CCAAGAAGGCCACAGAACTGAAACATCTTCAGTGTCTAGAAGAAGAACTC       350
AAACCTCTGGAGGAAGTGCTAAATTTAGCTCAAAGCAAAAACTTTCACTT       400
AAGACCCAGGGACTTAATCAGCAATATCAACGTAATAGTTCTGGAACTAA       450
AGGGATCTGAAACAACATTCATGTGTGAATATGCTGATGAGACAGCAACC       500
ATTGTAGAATTTCTGAACAGATGGATTACCTTTTGTCAAAGCATCATCTC       550
AACACTAACTTGATAACCAAGCAGAAAGTGGTACTAACCTTCTTCTCTTT       600
CTTCTCCTGACAGGACATACTGCTGAGGATGTCAAAAATGCAGTTGGAGT       650
CCTCATCGGAGGACTTGAATGGAATGATAACACAGTTCGAGTCTCTGAAA       700
CTCTACAGAGATTCGCTTGGAGAAGCAGTAATGAGAATGGGAGACCTCCA       750
CTCACTCCAAAACAGAAACGAGAAATGGCGGGAACAATTAGGTCAGAAGT       800
TTGAAGAAATAAGATGGTTGATTGAAGAAGTGAGACACAAACTGAAGATA       850
ACAGAGAATAGTTTTGAGCAAATAACATTTATGCAAGCCTTACATCTATT       900
GCTTGAAGTGGAGCAAGAGATAAGAACTTTCTCGTTTCAGCTTATTTAGT       950
ACTAAAAAACACCCTTGTTTCTACT                                975
```

Figure 1f

```
AGCAAAAGCAGGGTGACAAAGACATAATGGATCCAAACACTGTGTCAAGC        50
TTTCAGGTATTTGCCCTCCTGTGGGTGCTGCTGCTGTGGGTGCCCCGCAG       100
CCACGGCAACTGGGTGAACGTGATCAGCGACCTGAAGAAGATCGAGGACC       150
TGATCCAGAGCATGCACATCGACGCCACCCTGTACACCGAGAGCGACGTG       200
CACCCCAGCTGCAAGGTGACCGCCATGAAGTGCTTTCTGCTGGAACTGCA       250
GGTGATCAGCCTGGAAAGCGGCGACGCCAGCATCCACGACACCGTGGAGA       300
ACCTGATCATCCTGGCCAACAACAGCCTGAGCAGCAACGGCAACGTGACC       350
GAGAGCGGCTGCAAAGAGTGCGAGGAACTGGAAGAGAAGAACATCAAAGA       400
GTTTCTGCAGAGCTTCGTGCACATCGTGCAGATGTTCATCAACACCAGCT       450
GATGACCAAGCAGAAAGTGGTACTAACCTTCTTCTCTTTCTTCTCCTGAC       500
AGGACATACTGCTGAGGATGTCAAAAATGCAGTTGGAGTCCTCATCGGGG       550
GACTTGAATGGAATGATAACACAGTTCGAGTCTCTGAAACTCTACAGAGA       600
TTCGCTTGGAGAAGCAGTAATGAGAATGGGAGACCTCCACTCACTCCAAA       650
ACAGAAACGAGAAATGGCGGGAACAATTAGGTCAGAAGTTTGAAGAAATA       700
AGATGGTTGATTGAAGAAGTGAGACACAAACTGAAGATAACAGAGAATAG       750
TTTTGAGCAAATAACATTTATGCAAGCCTTACATCTATTGCTTGAAGTGG       800
AGCAAGAGATAAGAACTTTCTCGTTTCAGCTTATTTAATAATAAAAACA       850
CCCTTGTTTCTACT                                           864
```

Figure 1g

```
AGCAAAAGCAGGGTGACAAAGACATAATGGATCCAAACACTGTGTCAAGC      50
TTTCAGGTATTTGCCCTGCTGTGGGTGCTGCTCCTCTGGGTGCCCAGAAG     100
CCACGGAGCCCCTGCCAGAAGCCCCAGCCCCTCCACCCAGCCCTGGGAGC     150
ACGTGAACGCCATCCAGGAAGCCAGGCGGCTGCTGAACCTGAGCCGGGAC     200
ACAGCCGCCGAGATGAACGAGACCGTGGAGGTGATCAGCGAGATGTTCGA     250
CCTCCAGGAACCCACCTGCCTGCAGACCCGGCTGGAACTGTACAAGCAGG     300
GCCTGCGGGCAGCCTGACCAAGCTGAAGGGCCCCCTGACCATGATGGCC     350
AGCCACTACAAGCAGCACTGCCCCCCCACCCCGAGACCAGCTGCGCCAC     400
CCAGATCATCACCTTCGAGAGCTTCAAAGAGAACCTGAAGGACTTCCTGC     450
TGGTGATCCCCTTCGACTGCTGGGAGCCCGTGCAGGAATGATGACCAAGC     500
AGAAAGTGGTACTAACCTTCTTCTCTTTCTTCTCCTGACAGGACATACTG     550
CTGAGGATGTCAAAAATGCAGTTGGAGTCCTCATCGGGGACTTGAATGG     600
AATGATAACACAGTTCGAGTCTCTGAAACTCTACAGAGATTCGCTTGGAG     650
AAGCAGTAATGAGAATGGGAGACCTCCACTCACTCCAAAACAGAAACGAG     700
AAATGGCGGGAACAATTAGGTCAGAAGTTTGAAGAAATAAGATGGTTGAT     750
TGAAGAAGTGAGACACAAACTGAAGATAACAGAGAATAGTTTTGAGCAAA     800
TAACATTTATGCAAGCCTTACATCTATTGCTTGAAGTGGAGCAAGAGATA     850
AGAACTTTCTCGTTTCAGCTTATTTAATAATAAAAACACCCTTGTTTCT     900
ACT                                                    903
```

Figure 1h

```
AGCAAAAGCAGGGTGACAAAGACATAATGGATCCAAACACTGTGTCAAGC        50
TTTCAGGTATTTGCCCTGCTGTGGGTGCTGCTCCTCTGGGTGCCCAGAAG       100
CCACGGAGCCCCCTGGCCGCCGATACCCCCACCGCCTGCTGCTTCAGCT        150
ACACCAGCCGGCAGATCCCCCAGAACTTCATCGCCGACTACTTCGAGACC       200
AGCAGCCAGTGCAGCAAGCCCAGCGTGATCTTCCTGACCAAGCGGGGCAG       250
GCAGGTCTGCGCCGACCCCAGCGAGGAATGGGTGCAGAAATACGTGAGCG       300
ACCTGGAACTGAGCGCCTGATGACCAAGCAGAAAGTGGTACTAACCTTCT       350
TCTCTTTCTTCTCCTGACAGGACATACTGCTGAGGATGTCAAAAATGCAG       400
TTGGAGTCCTCATCGGGGACTTGAATGGAATGATAACACAGTTCGAGTC        450
TCTGAAACTCTACAGAGATTCGCTTGGAGAAGCAGTAATGAGAATGGGAG       500
ACCTCCACTCACTCCAAAACAGAAACGAGAAATGGCGGGAACAATTAGGT       550
CAGAAGTTTGAAGAAATAAGATGGTTGATTGAAGAAGTGAGACACAAACT       600
GAAGATAACAGAGAATAGTTTTGAGCAAATAACATTTATGCAAGCCTTAC       650
ATCTATTGCTTGAAGTGGAGCAAGAGATAAGAACTTTCTCGTTTCAGCTT       700
ATTTAATAATAAAAAACACCCTTGTTTCTACT                         732
```

Figure 1i

```
AGCAAAAGCAGGGTGACAAAGACATAATGGATCCAAACACTGTGTCAAGC      50
TTTCAGGTATTTGCCCTGCTGTGGGTGCTGCTCCTCTGGGTCCCCAGAAG     100
CCACGGCGCCAGCAACTTCGACTGCTGCCTGGGCTACACCGACCGGATCC     150
TGCACCCTAAGTTCATCGTGGGCTTCACCAGGCAGCTGGCCAACGAGGGC     200
TGCGACATCAACGCCATCATCTTCCACACCAAGAAAAAGCTGTCCGTGTG     250
CGCCAACCCCAAGCAGACCTGGGTGAAGTACATCGTGCGGCTGCTGTCCA     300
AGAAAGTGAAGAACATGTGATGACCAAGCAGAAAGTGGTACTAACCTTCT     350
TCTCTTTCTTCTCCTGACAGGACATACTGCTGAGGATGTCAAAAATGCAG     400
TTGGAGTCCTCATCGGGGACTTGAATGGAATGATAACACAGTTCGAGTC      450
TCTGAAACTCTACAGAGATTCGCTTGGAGAAGCAGTAATGAGAATGGGAG     500
ACCTCCACTCACTCCAAAACAGAAACGAGAAATGGCGGGAACAATTAGGT     550
CAGAAGTTTGAAGAAATAAGATGGTTGATTGAAGAAGTGAGACACAAACT     600
GAAGATAACAGAGAATAGTTTTGAGCAAATAACATTTATGCAAGCCTTAC     650
ATCTATTGCTTGAAGTGGAGCAAGAGATAAGAACTTTCTCGTTTCAGCTT     700
ATTTAATAATAAAAAACACCCTTGTTTCTACT                       732
```

Figure 1j

```
AGCAAAAGCAGGGTGACAAAGACATAATGGATCCAAACACTGTGTCAAGC      50
TTTCAGGTATTTGCCCTGCTCTGGGTGCTGCTGCTGTGGGTGCCCCGGTC     100
CCACGGCATGACCGAGCAGCAGTGGAACTTCGCCGGCATCGAGGCCGCCG     150
CTAGCGCCATCCAGGGCAACGTGACCAGCATCCACAGCCTGCTGGACGAG     200
GGCAAGCAGAGCCTGACCAAGCTGGCAGCTGCCTGGGCGGCTCTGGCAG     250
CGAGGCCTACCAGGGCGTGCAGCAGAAGTGGGACGCCACCGCCACCGAGC     300
TGAACAACGCCCTGCAGAACCTGGCCCGGACCATCAGCGAGGCCGGACAG     350
GCCATGGCCAGCACCGAGGGCAATGTGACAGGCATGTTCGCCTGATGACC     400
AAGCAGAAAGTGGTACTAACCTTCTTCTCTTTCTTCTCCTGACAGGACAT     450
ACTGCTGAGGATGTCAAAAATGCAGTTGGAGTCCTCATCGGGGACTTGA     500
ATGGAATGATAACACAGTTCGAGTCTCTGAAACTCTACAGAGATTCGCTT     550
GGAGAAGCAGTAATGAGAATGGGAGACCTCCACTCACTCCAAAACAGAAA     600
CGAGAAATGGCGGGAACAATTAGGTCAGAAGTTTGAAGAAATAAGATGGT     650
TGATTGAAGAAGTGAGACACAAACTGAAGATAACAGAGAATAGTTTTGAG     700
CAAATAACATTTATGCAAGCCTTACATCTATTGCTTGAAGTGGAGCAAGA     750
GATAAGAACTTTCTCGTTTCAGCTTATTTAATAATAAAAACACCCTTGT     800
TTCTACT                                                807
```

Figure 1k

```
AGCAAAAGCAGGGTGACAAAGACATAATGGATCCAAACACTGTGTCAAGC      50
TTTCAGGTATTTGCCATGACCGAGCAGCAGTGGAACTTCGCCGGCATCGA     100
GGCCGCAGCCAGCGCCATCCAGGGCAACGTGACCAGCATCCACAGCCTGC     150
TGGACGAGGGCAAGCAGAGCCTGACCAAGCTGGCCGCAGCCTGGGGCGGC     200
TCTGGCAGCGAGGCCTACCAGGGCGTGCAGCAGAAGTGGGACGCCACCGC     250
CACCGAGCTGAACAACGCCCTGCAGAACCTGGCCCGGACCATCAGCGAGG     300
CCGGACAGGCCATGGCCAGCACCGAGGGCAATGTGACAGGCATGTTCGCC     350
TGATGACCAAGCAGAAAGTGGTACTAACCTTCTTCTCTTTCTTCTCCTGA     400
CAGGACATACTGCTGAGGATGTCAAAAATGCAGTTGGAGTCCTCATCGGG     450
GGACTTGAATGGAATGATAACACAGTTCGAGTCTCTGAAACTCTACAGAG     500
ATTCGCTTGGAGAAGCAGTAATGAGAATGGGAGACCTCCACTCACTCCAA     550
AACAGAAACGAGAAATGGCGGGAACAATTAGGTCAGAAGTTTGAAGAAAT     600
AAGATGGTTGATTGAAGAAGTGAGACACAAACTGAAGATAACAGAGAATA     650
GTTTTGAGCAAATAACATTTATGCAAGCCTTACATCTATTGCTTGAAGTG     700
GAGCAAGAGATAAGAACTTTCTCGTTTCAGCTTATTTAATAATAAAAAAC     750
ACCCTTGTTTCTACT                                        765
```

Figure 1I

```
AGCAAAAGCAGGGTGACAAAAACATAATGGATCCAAACACTGTGTCAAGC      50
TTTCAGGTATTTGCCTGGGTGCTTTTCATACTTCTGCTTTTCCTGTTCCT     100
TCCAAGATCACATGGTGCACCTACTTCTTCGTCGACAAAGAAAACACAGC     150
TACAACTGGAGCATTTACTGCTGGATTTACAGATGATTTTGAATGGAATT     200
AATAATTACAAGAATCCCAAACTCACCAGGATGCTCACATTTAAGTTTTA     250
CATGCCCAAGAAGGCCACAGAACTGAAACATCTTCAGTGTCTAGAAGAAG     300
AACTCAAACCTCTGGAGGAAGTGCTAAATTTAGCTCAAAGCAAAAACTTT     350
CACTTAAGACCCAGGGACTTAATCAGCAATATCAACGTAATAGTTCTGGA     400
ACTAAAGGGATCTGAAACAACATTCATGTGTGAATATGCTGATGAGACAG     450
CAACCATTGTAGAATTTCTGAACAGATGGATTACCTTTTGTCAAAGCATC     500
ATCTCAACACTAACTTGATAACCAAGCAGAAAGTGGTACTAACCTTCTTC     550
TCTTTCTTCTCCTGACAGGACATACTGCTGAGGATGTCAAAAATGCAGTT     600
GGAGTCCTCATCGGGGACTTGAATGGAATGATAACACAGTTCGAGTCTC     650
TGAAACTCTACAGAGATTCGCTTGGAGAAGCAGTAATGAGAATGGGAGAC     700
CTCCACTCACTCCAAAACAGAAACGAGAAATGGCGGGAACAATTAGGTCA     750
GAAGTTTGAAGAAATAAGATGGTTGATTGAAGAAGTGAGACACAAACTGA     800
AGATAACAGAGAATAGTTTTGAGCAAATAACATTTATGCAAGCCTTACAT     850
CTATTGCTTGAAGTGGAGCAAGAGATAAGAACTTTCTCGTTTCAGCTTAT     900
TTAATAATAAAAAACACCCTTGTTTCTACT                         930
```

Figure 1m

```
AGCAAAAGCAGGGTGACAAAAACATAATGGATCCAAACACTGTGTCAAGC        50
TTTCAGGTATTTGCCGCAGGAGCTGCACTTTTGGCACTTCTTGCTGCACT       100
TCTTCCTGCTTCAAGAGCTGCACCTACTTCTTCGTCGACAAAGAAAACAC       150
AGCTACAACTGGAGCATTTACTGCTGGATTTACAGATGATTTTGAATGGA       200
ATTAATAATTACAAGAATCCCAAACTCACCAGGATGCTCACATTTAAGTT       250
TTACATGCCCAAGAAGGCCACAGAACTGAAACATCTTCAGTGTCTAGAAG       300
AAGAACTCAAACCTCTGGAGGAAGTGCTAAATTTAGCTCAAAGCAAAAAC       350
TTTCACTTAAGACCCAGGGACTTAATCAGCAATATCAACGTAATAGTTCT       400
GGAACTAAAGGGATCTGAAACAACATTCATGTGTGAATATGCTGATGAGA       450
CAGCAACCATTGTAGAATTTCTGAACAGATGGATTACCTTTTGTCAAAGC       500
ATCATCTCAACACTAACTTGATAACCAAGCAGAAAGTGGTACTAACCTTC       550
TTCTCTTTCTTCTCCTGACAGGACATACTGCTGAGGATGTCAAAAATGCA       600
GTTGGAGTCCTCATCGGGGACTTGAATGGAATGATAACACAGTTCGAGT       650
CTCTGAAACTCTACAGAGATTCGCTTGGAGAAGCAGTAATGAGAATGGGA       700
GACCTCCACTCACTCCAAAACAGAAACGAGAAATGGCGGGAACAATTAGG       750
TCAGAAGTTTGAAGAAATAAGATGGTTGATTGAAGAAGTGAGACACAAAC       800
TGAAGATAACAGAGAATAGTTTTGAGCAAATAACATTTATGCAAGCCTTA       850
CATCTATTGCTTGAAGTGGAGCAAGAGATAAGAACTTTCTCGTTTCAGCT       900
TATTTAATAATAAAAAACACCCTTGTTTCTACT                        933
```

Figure 1n

MDPNTVSSFQVDCFLWHVRKRVADQELGDAPFLDRLRRDQKSLRGRGSTLGLDIE
TATRAGKQIVERILKEESDEALKMTMASVPASRYLTDMTLEEMSRDWSMLIPKQKV
AGPLCIRMDQAIMDKNIILKANFSVIFDRLETLILLRAFTEEGAIVGEISPLPSLPGHTAE
DVKNAVGVLIGGLEWNDNTVRVSETLQRFAWRSSNENGRPPLTPKQKREMAGTIR
SEV

Figure 6

```
agcagaagcagaggatttgtttagtcactggcaaacaggaaaaaATGGCG      50
AACAACATGACCACAACACAAATTGAGGTGGGTCCGGGAGCAACCAATGC     100
CACCATAAACTTTGAAGCAGGAATTCTGGAGTGCTATGAAAGGCTTTCAT     150
GGCAAAGAtaatgtacaggatgcaactcctgtcttgcattgcactaagtc     200
ttgcacttgtcacaaacagtgcacctacttcttcgtcgacaagaaaaca     250
cagctacaactggagcatttactgctggatttacagatgattttgaatgg     300
aattaataattacaagaatcccaaactcaccaggatgctcacatttaagt     350
tttacatgcccaagaaggccacagaactgaaacatcttcagtgtctagaa     400
gaagaactcaaacctctggaggaagtgctaaatttagctcaaagcaaaaa     450
ctttcacttaagacccagggacttaatcagcaatatcaacgtaatagttc     500
tggaactaaagggatctgaaacaacattcatgtgtgaatatgctgatgag     550
acagcaaccattgtagaatttctgaacagatggattacctttgtcaaag     600
catcatctcaacactaacttgataaTACTAACCTTCTTCTCTTTCTTCTC     650
CTGACAGtggAGGATGAAGAAGATGGCCATCGGATCCTCAACTCACTCTT     700
CGAGCGTCTTAATGAAGGACATTCAAAGCCAATTCGAGCAGCTGAAACTG     750
CGGTGGGAGTCTTATCCCAATTTGGTCAAGAGCACCGATTATCACCAGAA     800
GAGGGAGACAATTAGACTGGTCACGGAAGAACTTTATCTTTTAAGTAAAA     850
GAATTGATGATAACATATTATTCCACAAAACAGTAATAGCTAACAGCTCC     900
ATAATAGCTGACATGGTTGTATCATTATCATTATTAGAAACATTGTATGA     950
AATGAAGGATGTGGTTGAAGTGTACAGCAGGCAGTGCTTGTGAatttaaa    1000
ataaaaatcctcttgttactact                              1023
```

Figure 9

SEQUENCE LISTING

<160> NUMBER OF SEQ ID NOS: 82

<210> SEQ ID NO 1
<211> LENGTH: 1101
<212> TYPE: DNA
<213> ORGANISM: human

<400> SEQUENCE: 1
agcaaaagca gggtgacaaa aacataatgg atccaaacac tgtgtcaagc tttcaggtaa      60
gtatctttct ttggcgtgtc cgcaaacgat aatgtacagg atgcaactcc tgtcttgcat     120
tgcactaagt cttgcacttg tcacaaacag tgcacctact tcttcgtcga caaagaaaac     180

| | |
|---|---|
| acagctacaa ctggagcatt tactgctgga tttacagatg attttgaatg gaattaataa | 240 |
| ttacaagaat cccaaactca ccaggatgct cacatttaag ttttacatgc ccaagaaggc | 300 |
| cacagaactg aaacatcttc agtgtctaga agaagaactc aaacctctgg aggaagtgct | 360 |
| aaatttagct caaagcaaaa actttcactt aagacccagg gacttaatca gcaatatcaa | 420 |
| cgtaatagtt ctggaactaa agggatctga aacaacattc atgtgtgaat atgctgatga | 480 |
| gacagcaacc attgtagaat ttctgaacag atggattacc ttttgtcaaa gcatcatctc | 540 |
| aacactaact tgataaccaa gcagaaagtg gcaggccctc tttgtatcag aatggaccag | 600 |
| gcgatcatgg ataagaacat catactgaaa gcgaacttca gtgtgatttt tgaccggctg | 660 |
| gagactctaa tattgctaag ggctttcacc gaagagggag caattgttgg cgaaatttca | 720 |
| ccattgcctt ctcttccagg acatactgct gaggatgtca aaaatgcagt ggagtcctc | 780 |
| atcgggggac ttgaatggaa tgataacaca gttcgagtct ctgaaactct acagagattc | 840 |
| gcttggagaa gcagtaatga gaatgggaga cctccactca ctccaaaaca gaaacgagaa | 900 |
| atggcgggaa caattaggtc agaagtttga agaaataaga tggttgattg aagaagtgag | 960 |
| acacaaactg aagataacag agaatagttt tgagcaaata acatttatgc aagccttaca | 1020 |
| tctattgctt gaagtggagc aagagataag aactttctcg tttcagctta tttaataata | 1080 |
| aaaaacaccc ttgtttctac t | 1101 |

<210> SEQ ID NO 2
<211> LENGTH: 965
<212> TYPE: DNA
<213> ORGANISM: human

<400> SEQUENCE: 2

| | |
|---|---|
| agcaaaagca gggtgacaaa aacataatgg atccaaacac tgtgtcaagc tttcaggtaa | 60 |
| gtatctttct ttggcgtgtc cgcaaacgat aatgtacagg atgcaactcc tgtcttgcat | 120 |
| tgcactaagt cttgcacttg tcacaaacag tgcacctact tcttcgtcga caaagaaaac | 180 |
| acagctacaa ctggagcatt tactgctgga tttacagatg attttgaatg gaattaataa | 240 |
| ttacaagaat cccaaactca ccaggatgct cacatttaag ttttacatgc ccaagaaggc | 300 |
| cacagaactg aaacatcttc agtgtctaga agaagaactc aaacctctgg aggaagtgct | 360 |
| aaatttagct caaagcaaaa actttcactt aagacccagg gacttaatca gcaatatcaa | 420 |
| cgtaatagtt ctggaactaa agggatctga aacaacattc atgtgtgaat atgctgatga | 480 |
| gacagcaacc attgtagaat ttctgaacag atggattacc ttttgtcaaa gcatcatctc | 540 |
| aacactaact tgataaccaa gcagaaagtg gtactaacct tcttctcttt cttctcctga | 600 |
| caggacatac tgctgaggat gtcaaaaatg cagttggagt cctcatcggg ggacttgaat | 660 |
| ggaatgataa cacagttcga gtctctgaaa ctctacagag attcgcttgg agaagcagta | 720 |
| atgagaatgg gagacctcca ctcactccaa aacagaaacg agaaatggcg ggaacaatta | 780 |
| ggtcagaagt ttgaagaaat aagatggttg attgaagaag tgagacacaa actgaagata | 840 |
| acagagaata gttttgagca aataacattt atgcaagcct tacatctatt gcttgaagtg | 900 |
| gagcaagaga taagaacttt ctcgtttcag cttatttaat aataaaaaac accttgtttt | 960 |
| ctact | 965 |

<210> SEQ ID NO 3
<211> LENGTH: 921
<212> TYPE: DNA
<213> ORGANISM: human

<400> SEQUENCE: 3

```
agcaaaagca gggtgacaaa acataatgg atccaaacac tgtgtcaagc tttcaggtaa      60
gtctcctgct ttgggtactg ctgctctggg ttccaggttc cactggtgca cctacttctt    120
cgtcgacaaa gaaaacacag ctacaactgg agcatttact gctggattta cagatgattt    180
tgaatggaat taataattac aagaatccca aactcaccag gatgctcaca tttaagtttt    240
acatgcccaa gaaggccaca gaactgaaac atcttcagtg tctagaagaa gaactcaaac    300
ctctggagga agtgctaaat ttagctcaaa gcaaaaactt tcacttaaga cccagggact    360
taatcagcaa tatcaacgta atagttctgg aactaaaggg atctgaaaca acattcatgt    420
gtgaatatgc tgatgagaca gcaaccattg tagaatttct gaacagatgg attacctttt    480
gtcaaagcat catctcaaca ctaacttgat aaccaagcag aaagtggtac taaccttctt    540
ctctttcttc tcctgacagg acatactgct gaggatgtca aaaatgcagt tggagtcctc    600
atcggggac ttgaatggaa tgataacaca gttcgagtct ctgaaactct acagagattc    660
gcttggagaa gcagtaatga gaatgggaga cctccactca ctccaaaaca gaaacgagaa    720
atggcgggaa caattaggtc agaagtttga agaaataaga tggttgattg aagaagtgag    780
acacaaactg aagataacag agaatagttt tgagcaaata acatttatgc aagccttaca    840
tctattgctt gaagtggagc aagagataag aactttctcg tttcagctta tttaataata    900
aaaaacaccc ttgtttctac t                                              921
```

<210> SEQ ID NO 4
<211> LENGTH: 965
<212> TYPE: DNA
<213> ORGANISM: human

<400> SEQUENCE: 4

```
agcaaaagca gggtgacaaa acataatgg atccaaacac tgtgtcaagc tttcaggtag      60
attgctttct ttggcgtgtc cgcaaacgat aatgtacagg atgcaactcc tgtcttgcat    120
tgcactaagt cttgcacttg tcacaaacag tgcacctact tcttcgtcga caaagaaaac    180
acagctacaa ctggagcatt tactgctgga tttacagatg attttgaatg gaattaataa    240
ttacaagaat cccaaactca ccaggatgct cacatttaag ttttacatgc ccaagaaggc    300
cacagaactg aaacatcttc agtgtctaga agaagaactc aaacctctgg aggaagtgct    360
aaatttagct caaagcaaaa actttcactt aagacccagg gacttaatca gcaatatcaa    420
cgtaatagtt ctgaactaa agggatctga acaacattc atgtgtgaat atgctgatga    480
gacagcaacc attgtagaat tctgaacag atggattacc ttttgtcaaa gcatcatctc    540
aacactaact tgataaccaa gcagaaagtg gtactaacct tcttctcttt cttctcctga    600
caggacatac tgctgaggat gtcaaaaatg cagttggagt cctcatcggg ggacttgaat    660
ggaatgataa cacagttcga gtctctgaaa ctctacagag attcgcttgg agaagcagta    720
atgagaatgg gagacctcca ctcactccaa aacagaaacg agaaatggcg ggaacaatta    780
ggtcagaagt ttgaagaaat aagatggttg attgaagaag tgagacacaa actgaagata    840
acagagaata gttttgagca aataacattt atgcaagcct acatctatt gcttgaagtg    900
gagcaagaga taagaacttt ctcgtttcag cttatttagt actaaaaaac cccttgtttt    960
ctact                                                                965
```

<210> SEQ ID NO 5

```
<211> LENGTH: 921
<212> TYPE: DNA
<213> ORGANISM: human

<400> SEQUENCE: 5
agcaaaagca gggtgacaaa acataatgg atccaaacac tgtgtcaagc tttcaggtat      60
ttgccctgct ttgggtactg ctgctctggg ttccaggttc cactggtgca cctacttctt    120
cgtcgacaaa gaaaacacag ctacaactgg agcatttact gctggattta cagatgattt    180
tgaatggaat taataattac aagaatccca aactcaccag gatgctcaca tttaagtttt    240
acatgcccaa gaaggccaca gaactgaaac atcttcagtg tctagaagaa gaactcaaac    300
ctctggagga agtgctaaat ttagctcaaa gcaaaaactt tcacttaaga cccagggact    360
taatcagcaa tatcaacgta atagttctgg aactaaaggg atctgaaaca acattcatgt    420
gtgaatatgc tgatgagaca gcaaccattg tagaatttct gaacagatgg attaccttt    480
gtcaaagcat catctcaaca ctaacttgat aaccaagcag aaagtggtac taaccttctt    540
ctctttcttc tcctgacagg acatactgct gaggatgtca aaaatgcagt ggagtcctc    600
atcggggac ttgaatggaa tgataacaca gttcgagtct ctgaaactct acagagattc    660
gcttggagaa gcagtaatga gaatgggaga cctccactca ctccaaaaca gaaacgagaa    720
atggcgggaa caattaggtc agaagtttga agaaataaga tggttgattg aagaagtgag    780
acacaaactg aagataacag agaatagttt tgagcaaata acatttatgc aagccttaca    840
tctattgctt gaagtggagc aagagataag aactttctcg tttcagctta tttaataata    900
aaaaacaccc ttgtttctac t                                              921

<210> SEQ ID NO 6
<211> LENGTH: 975
<212> TYPE: DNA
<213> ORGANISM: human

<400> SEQUENCE: 6
agcaaaagca gggtgacaaa acataatgg atccaaacac tgtgtcaagc tttcaggtaa      60
gtatctttct ttggcgtgtc cgcaaacgat aagccgccac catgtacagg atgcaactcc    120
tgtcttgcat tgcactaagt cttgcacttg tcacaaacag tgcacctact tcttcgtcga    180
caaagaaaac acagctacaa ctggagcatt tactgctgga tttacagatg attttgaatg    240
gaattaataa ttacaagaat cccaaactca ccaggatgct cacatttaag ttttacatgc    300
ccaagaaggc cacagaactg aaacatcttc agtgtctaga agaagaactc aaacctctgg    360
aggaagtgct aaatttagct caaagcaaaa actttcactt aagacccagg gacttaatca    420
gcaatatcaa cgtaatagtt ctggaactaa agggatctga acaacattc atgtgtgaat    480
atgctgatga gacagcaacc attgtagaat ttctgaacag atggattacc ttttgtcaaa    540
gcatcatctc aacactaact tgataaccaa gcagaaagtg gtactaacct tcttctcttt    600
cttctcctga caggacatac tgctgaggat gtcaaaaatg cagttggagt cctcatcgga    660
ggacttgaat ggaatgataa cacagttcga gtctctgaaa ctctacagag attcgcttgg    720
agaagcagta atgagaatgg gagacctcca ctcactccaa aacagaaacg agaaatggcg    780
ggaacaatta ggtcagaagt ttgaagaaat aagatggttg attgaagaag tgagacacaa    840
actgaagata acagagaata gttttgagca aataacattt atgcaagcct tacatctatt    900
gcttgaagtg gagcaagaga taagaacttt ctcgtttcag cttatttagt actaaaaaac    960
acccttgttt ctact                                                     975
```

<210> SEQ ID NO 7
<211> LENGTH: 864
<212> TYPE: DNA
<213> ORGANISM: human

<400> SEQUENCE: 7

| | | | | | |
|---|---|---|---|---|---|
| agcaaaagca | gggtgacaaa | gacataatgg | atccaaacac | tgtgtcaagc | tttcaggtat | 60 |
| ttgccctcct | gtgggtgctg | ctgctgtggg | tgccccgcag | ccacggcaac | tgggtgaacg | 120 |
| tgatcagcga | cctgaagaag | atcgaggacc | tgatccagag | catgcacatc | gacgccaccc | 180 |
| tgtacaccga | gagcgacgtg | caccccagct | gcaaggtgac | cgccatgaag | tgctttctgc | 240 |
| tggaactgca | ggtgatcagc | ctggaaagcg | gcgacgccag | catccacgac | accgtggaga | 300 |
| acctgatcat | cctggccaac | aacagcctga | gcagcaacgg | caacgtgacc | gagagcggct | 360 |
| gcaaagagtg | cgaggaactg | gaagagaaga | acatcaaaga | gtttctgcag | agcttcgtgc | 420 |
| acatcgtgca | gatgttcatc | aacaccagct | gatgaccaag | cagaaagtgg | tactaacctt | 480 |
| cttctctttc | ttctcctgac | aggacatact | gctgaggatg | tcaaaaatgc | agttggagtc | 540 |
| ctcatcgggg | gacttgaatg | gaatgataac | acagttcgag | tctctgaaac | tctacagaga | 600 |
| ttcgcttgga | gaagcagtaa | tgagaatggg | agacctccac | tcactccaaa | acagaaacga | 660 |
| gaaatggcgg | gaacaattag | gtcagaagtt | tgaagaaata | agatggttga | ttgaagaagt | 720 |
| gagacacaaa | ctgaagataa | cagagaatag | ttttgagcaa | ataacattta | tgcaagcctt | 780 |
| acatctattg | cttgaagtgg | agcaagagat | aagaactttc | tcgtttcagc | ttatttaata | 840 |
| ataaaaaaca | cccttgtttc | tact | | | | 864 |

<210> SEQ ID NO 8
<211> LENGTH: 903
<212> TYPE: DNA
<213> ORGANISM: human

<400> SEQUENCE: 8

| | | | | | |
|---|---|---|---|---|---|
| agcaaaagca | gggtgacaaa | gacataatgg | atccaaacac | tgtgtcaagc | tttcaggtat | 60 |
| ttgccctgct | gtgggtgctg | ctcctctggg | tgccagaagc | cacggagcc | cctgccagaa | 120 |
| gccccagccc | ctccacccag | ccctgggagc | acgtgaacgc | catccaggaa | gccaggcggc | 180 |
| tgctgaacct | gagccgggac | acagccgccg | agatgaacga | gaccgtggag | gtgatcagcg | 240 |
| agatgttcga | cctccaggaa | cccacctgcc | tgcagacccg | gctggaactg | tacaagcagg | 300 |
| gcctgcgggg | cagcctgacc | aagctgaagg | gcccctgac | catgatggcc | agccactaca | 360 |
| agcagcactg | cccccccacc | cccgagacca | gctgcgccac | ccagatcatc | accttcgaga | 420 |
| gcttcaaaga | gaacctgaag | gacttcctgc | tggtgatccc | cttcgactgc | tgggagcccg | 480 |
| tgcaggaatg | atgaccaagc | agaaagtggt | actaaccttc | ttctctttct | tctcctgaca | 540 |
| ggacatactg | ctgaggatgt | caaaaatgca | gttggagtcc | tcatcggggg | acttgaatgg | 600 |
| aatgataaca | cagttcgagt | ctctgaaact | ctacagagat | tcgcttggag | aagcagtaat | 660 |
| gagaatggga | gacctccact | cactccaaaa | cagaaacgag | aaatggcggg | aacaattagg | 720 |
| tcagaagttt | gaagaaataa | gatggttgat | tgaagaagtg | agacacaaac | tgaagataac | 780 |
| agagaatagt | tttgagcaaa | taacatttat | gcaagcctta | catctattgc | ttgaagtgga | 840 |
| gcaagagata | agaactttct | cgtttcagct | tatttaataa | taaaaaacac | ccttgtttct | 900 |
| act | | | | | | 903 |

<210> SEQ ID NO 9
<211> LENGTH: 732
<212> TYPE: DNA
<213> ORGANISM: human

<400> SEQUENCE: 9

| | | | | | |
|---|---|---|---|---|---|
| agcaaaagca | gggtgacaaa | gacataatgg | atccaaacac | tgtgtcaagc | tttcaggtat | 60 |
| ttgccctgct | gtgggtgctg | ctcctctggg | tgcccagaag | ccacggagcc | ccctggccg | 120 |
| ccgatacccc | caccgcctgc | tgcttcagct | acaccagccg | gcagatcccc | cagaacttca | 180 |
| tcgccgacta | cttcgagacc | agcagccagt | gcagcaagcc | cagcgtgatc | ttcctgacca | 240 |
| agcggggcag | gcaggtctgc | gccgacccca | gcgaggaatg | ggtgcagaaa | tacgtgagcg | 300 |
| acctggaact | gagcgcctga | tgaccaagca | gaaagtggta | ctaaccttct | tctctttctt | 360 |
| ctcctgacag | gacatactgc | tgaggatgtc | aaaaatgcag | ttggagtcct | catcggggga | 420 |
| cttgaatgga | atgataacac | agttcgagtc | tctgaaactc | tacagagatt | cgcttggaga | 480 |
| agcagtaatg | agaatgggag | acctccactc | actccaaaac | agaaacgaga | aatggcggga | 540 |
| acaattaggt | cagaagtttg | aagaaataag | atggttgatt | gaagaagtga | gacacaaact | 600 |
| gaagataaca | gagaatagtt | ttgagcaaat | aacatttatg | caagccttac | atctattgct | 660 |
| tgaagtggag | caagagataa | gaactttctc | gtttcagctt | atttaataat | aaaaaacacc | 720 |
| cttgttttcta | ct | | | | | 732 |

<210> SEQ ID NO 10
<211> LENGTH: 732
<212> TYPE: DNA
<213> ORGANISM: human

<400> SEQUENCE: 10

| | | | | | |
|---|---|---|---|---|---|
| agcaaaagca | gggtgacaaa | gacataatgg | atccaaacac | tgtgtcaagc | tttcaggtat | 60 |
| ttgccctgct | gtgggtgctg | ctcctctggg | tcccagaag | ccacggcgcc | agcaacttcg | 120 |
| actgctgcct | gggctacacc | gaccggatcc | tgcaccctaa | gttcatcgtg | ggcttcacca | 180 |
| ggcagctggc | caacgagggc | tgcgacatca | cgccatcat | cttccacacc | aagaaaaagc | 240 |
| tgtccgtgtg | cgccaacccc | aagcagacct | gggtgaagta | catcgtgcgg | ctgctgtcca | 300 |
| agaaagtgaa | gaacatgtga | tgaccaagca | gaaagtggta | ctaaccttct | tctctttctt | 360 |
| ctcctgacag | gacatactgc | tgaggatgtc | aaaaatgcag | ttggagtcct | catcggggga | 420 |
| cttgaatgga | atgataacac | agttcgagtc | tctgaaactc | tacagagatt | cgcttggaga | 480 |
| agcagtaatg | agaatgggag | acctccactc | actccaaaac | agaaacgaga | aatggcggga | 540 |
| acaattaggt | cagaagtttg | aagaaataag | atggttgatt | gaagaagtga | gacacaaact | 600 |
| gaagataaca | gagaatagtt | ttgagcaaat | aacatttatg | caagccttac | atctattgct | 660 |
| tgaagtggag | caagagataa | gaactttctc | gtttcagctt | atttaataat | aaaaaacacc | 720 |
| cttgttttcta | ct | | | | | 732 |

<210> SEQ ID NO 11
<211> LENGTH: 21
<212> TYPE: PRT
<213> ORGANISM: mouse

<400> SEQUENCE: 11

Met Glu Thr Asp Thr Leu Leu Leu Trp Val Leu Leu Leu Trp Val Pro
1               5                   10                  15

```
Gly Ser Thr Gly Asp
            20

<210> SEQ ID NO 12
<211> LENGTH: 17
<212> TYPE: PRT
<213> ORGANISM: Human endogenous retrovirus

<400> SEQUENCE: 12

Glu Met Gln Arg Lys Ala Pro Pro Arg Arg Arg His Arg Asn Arg
1               5                   10                  15

Ala

<210> SEQ ID NO 13
<211> LENGTH: 17
<212> TYPE: PRT
<213> ORGANISM: Human endogenous retrovirus

<400> SEQUENCE: 13

Arg Met Lys Leu Pro Ser Thr Lys Lys Ala Glu Pro Pro Thr Trp Ala
1               5                   10                  15

Gln

<210> SEQ ID NO 14
<211> LENGTH: 17
<212> TYPE: PRT
<213> ORGANISM: Human endogenous retrovirus

<400> SEQUENCE: 14

Thr Lys Lys Ala Glu Pro Pro Thr Trp Ala Gln Leu Lys Lys Leu Thr
1               5                   10                  15

Gln

<210> SEQ ID NO 15
<211> LENGTH: 17
<212> TYPE: PRT
<213> ORGANISM: Human endogenous retrovirus

<400> SEQUENCE: 15

Met Pro Ala Gly Ala Ala Ala Ala Asn Tyr Thr Tyr Trp Ala Tyr Val
1               5                   10                  15

Pro

<210> SEQ ID NO 16
<211> LENGTH: 17
<212> TYPE: PRT
<213> ORGANISM: Human endogenous retrovirus

<400> SEQUENCE: 16

Pro Ile Asp Asp Arg Cys Pro Ala Lys Pro Glu Glu Glu Gly Met Met
1               5                   10                  15

Ile

<210> SEQ ID NO 17
<211> LENGTH: 17
<212> TYPE: PRT
<213> ORGANISM: Human endogenous retrovirus

<400> SEQUENCE: 17

Tyr Pro Pro Ile Cys Leu Gly Arg Ala Pro Gly Cys Leu Met Pro Ala
1               5                   10                  15
```

Val

<210> SEQ ID NO 18
<211> LENGTH: 17
<212> TYPE: PRT
<213> ORGANISM: Human endogenous retrovirus

<400> SEQUENCE: 18

Tyr Gln Arg Ser Leu Lys Phe Arg Pro Lys Gly Lys Pro Cys Pro Lys
1               5                   10                  15

Glu

<210> SEQ ID NO 19
<211> LENGTH: 17
<212> TYPE: PRT
<213> ORGANISM: Human endogenous retrovirus

<400> SEQUENCE: 19

Phe Arg Pro Lys Gly Lys Pro Cys Pro Lys Glu Ile Pro Lys Glu Ser
1               5                   10                  15

Lys

<210> SEQ ID NO 20
<211> LENGTH: 17
<212> TYPE: PRT
<213> ORGANISM: Human endogenous retrovirus

<400> SEQUENCE: 20

Gly Lys Pro Cys Pro Lys Glu Ile Pro Lys Glu Ser Lys Asn Thr Glu
1               5                   10                  15

Val

<210> SEQ ID NO 21
<211> LENGTH: 17
<212> TYPE: PRT
<213> ORGANISM: Human endogenous retrovirus

<400> SEQUENCE: 21

Gly Thr Ile Ile Asp Trp Ala Pro Arg Gly Gln Phe Tyr His Asn Cys
1               5                   10                  15

Ser

<210> SEQ ID NO 22
<211> LENGTH: 17
<212> TYPE: PRT
<213> ORGANISM: Human endogenous retrovirus

<400> SEQUENCE: 22

Arg Gly Gln Phe Tyr His Asn Cys Ser Gly Gln Thr Gln Ser Cys Pro
1               5                   10                  15

Ser

<210> SEQ ID NO 23
<211> LENGTH: 17
<212> TYPE: PRT
<213> ORGANISM: Human endogenous retrovirus

<400> SEQUENCE: 23

Asp Leu Thr Glu Ser Leu Asp Lys His Lys His Lys Lys Leu Gln Ser
1               5                   10                  15

Phe

<210> SEQ ID NO 24
<211> LENGTH: 17
<212> TYPE: PRT
<213> ORGANISM: Human endogenous retrovirus

<400> SEQUENCE: 24

Pro Trp Gly Trp Gly Glu Lys Gly Ile Ser Thr Pro Arg Pro Lys Ile
1               5                   10                  15
Val

<210> SEQ ID NO 25
<211> LENGTH: 17
<212> TYPE: PRT
<213> ORGANISM: Human endogenous retrovirus

<400> SEQUENCE: 25

Pro Lys Ile Val Ser Pro Val Ser Gly Pro Glu His Pro Glu Leu Trp
1               5                   10                  15
Arg

<210> SEQ ID NO 26
<211> LENGTH: 16
<212> TYPE: PRT
<213> ORGANISM: Human endogenous retrovirus

<400> SEQUENCE: 26

Pro Arg Val Asn Tyr Leu Gln Asp Phe Ser Gln Arg Ser Leu Lys Phe
1               5                   10                  15

<210> SEQ ID NO 27
<211> LENGTH: 17
<212> TYPE: PRT
<213> ORGANISM: Human endogenous retrovirus

<400> SEQUENCE: 27

Arg Val Asn Tyr Leu Gln Asp Phe Ser Tyr Gln Arg Ser Leu Lys Phe
1               5                   10                  15
Arg

<210> SEQ ID NO 28
<211> LENGTH: 17
<212> TYPE: PRT
<213> ORGANISM: Human endogenous retrovirus

<400> SEQUENCE: 28

Val Asn Tyr Leu Gln Asp Phe Ser Tyr Gln Arg Ser Leu Lys Phe Arg
1               5                   10                  15
Pro

<210> SEQ ID NO 29
<211> LENGTH: 18
<212> TYPE: PRT
<213> ORGANISM: Human endogenous retrovirus

<400> SEQUENCE: 29

Val Asn Tyr Leu Gln Asp Phe Ser Tyr Gln Arg Ser Leu Lys Phe Arg
1               5                   10                  15
Ser Pro

<210> SEQ ID NO 30

<211> LENGTH: 17
<212> TYPE: PRT
<213> ORGANISM: Human endogenous retrovirus

<400> SEQUENCE: 30

Asn Tyr Leu Gln Asp Phe Ser Tyr Gln Arg Ser Leu Lys Phe Arg Pro
1               5                   10                  15
Lys

<210> SEQ ID NO 31
<211> LENGTH: 18
<212> TYPE: PRT
<213> ORGANISM: Human endogenous retrovirus

<400> SEQUENCE: 31

Tyr Leu Gln Asp Phe Ser Tyr Gln Arg Ser Leu Lys Phe Arg Pro Lys
1               5                   10                  15
Gly Lys

<210> SEQ ID NO 32
<211> LENGTH: 17
<212> TYPE: PRT
<213> ORGANISM: Human endogenous retrovirus

<400> SEQUENCE: 32

Leu Gln Asp Phe Ser Tyr Gln Arg Ser Leu Lys Phe Arg Pro Lys Gly
1               5                   10                  15
Lys

<210> SEQ ID NO 33
<211> LENGTH: 17
<212> TYPE: PRT
<213> ORGANISM: Human endogenous retrovirus

<400> SEQUENCE: 33

Gln Asp Phe Ser Tyr Gln Arg Ser Leu Lys Phe Arg Pro Lys Gly Lys
1               5                   10                  15
Pro

<210> SEQ ID NO 34
<211> LENGTH: 17
<212> TYPE: PRT
<213> ORGANISM: Human endogenous retrovirus

<400> SEQUENCE: 34

Asp Phe Ser Tyr Gln Arg Ser Leu Lys Phe Arg Pro Lys Gly Lys Pro
1               5                   10                  15
Cys

<210> SEQ ID NO 35
<211> LENGTH: 17
<212> TYPE: PRT
<213> ORGANISM: Human endogenous retrovirus

<400> SEQUENCE: 35

Phe Ser Tyr Gln Arg Ser Leu Lys Phe Arg Pro Lys Gly Lys Pro Cys
1               5                   10                  15
Pro

<210> SEQ ID NO 36
<211> LENGTH: 17

-continued

<212> TYPE: PRT
<213> ORGANISM: Human endogenous retrovirus

<400> SEQUENCE: 36

Ser Tyr Gln Arg Ser Leu Lys Phe Arg Pro Lys Gly Lys Pro Cys Pro
1               5                   10                  15

Lys

<210> SEQ ID NO 37
<211> LENGTH: 17
<212> TYPE: PRT
<213> ORGANISM: Human endogenous retrovirus

<400> SEQUENCE: 37

Tyr Gln Arg Ser Leu Lys Phe Arg Pro Lys Gly Lys Pro Cys Pro Lys
1               5                   10                  15

Glu

<210> SEQ ID NO 38
<211> LENGTH: 17
<212> TYPE: PRT
<213> ORGANISM: Human endogenous retrovirus

<400> SEQUENCE: 38

Gln Arg Ser Leu Lys Phe Arg Pro Lys Gly Lys Pro Cys Pro Lys Glu
1               5                   10                  15

Ile

<210> SEQ ID NO 39
<211> LENGTH: 17
<212> TYPE: PRT
<213> ORGANISM: Human endogenous retrovirus

<400> SEQUENCE: 39

Arg Ser Leu Lys Phe Arg Pro Lys Gly Lys Pro Cys Pro Lys Glu Ile
1               5                   10                  15

Pro

<210> SEQ ID NO 40
<211> LENGTH: 17
<212> TYPE: PRT
<213> ORGANISM: Human endogenous retrovirus

<400> SEQUENCE: 40

Ser Leu Lys Phe Arg Pro Lys Gly Lys Pro Cys Pro Lys Glu Ile Pro
1               5                   10                  15

Lys

<210> SEQ ID NO 41
<211> LENGTH: 17
<212> TYPE: PRT
<213> ORGANISM: Human endogenous retrovirus

<400> SEQUENCE: 41

Leu Lys Phe Arg Pro Lys Gly Lys Pro Cys Pro Lys Glu Ile Pro Lys
1               5                   10                  15

Glu

<210> SEQ ID NO 42
<211> LENGTH: 17
<212> TYPE: PRT

<210> SEQ ID NO 42
<211> LENGTH: 17
<212> TYPE: PRT
<213> ORGANISM: Human endogenous retrovirus

<400> SEQUENCE: 42

Lys Phe Arg Pro Lys Gly Lys Pro Cys Pro Lys Glu Ile Pro Lys Glu
1               5                   10                  15
Ser

<210> SEQ ID NO 43
<211> LENGTH: 17
<212> TYPE: PRT
<213> ORGANISM: Human endogenous retrovirus

<400> SEQUENCE: 43

Phe Arg Pro Lys Gly Lys Pro Cys Pro Lys Glu Ile Pro Lys Glu Ser
1               5                   10                  15
Lys

<210> SEQ ID NO 44
<211> LENGTH: 17
<212> TYPE: PRT
<213> ORGANISM: Human endogenous retrovirus

<400> SEQUENCE: 44

Arg Pro Lys Gly Lys Pro Cys Pro Lys Glu Ile Pro Lys Glu Ser Lys
1               5                   10                  15
Asn

<210> SEQ ID NO 45
<211> LENGTH: 17
<212> TYPE: PRT
<213> ORGANISM: Human endogenous retrovirus

<400> SEQUENCE: 45

Pro Lys Gly Lys Pro Cys Pro Lys Glu Ile Pro Lys Glu Ser Lys Asn
1               5                   10                  15
Thr

<210> SEQ ID NO 46
<211> LENGTH: 17
<212> TYPE: PRT
<213> ORGANISM: Human endogenous retrovirus

<400> SEQUENCE: 46

Lys Gly Lys Pro Cys Pro Lys Glu Ile Pro Lys Glu Ser Lys Asn Thr
1               5                   10                  15
Glu

<210> SEQ ID NO 47
<211> LENGTH: 17
<212> TYPE: PRT
<213> ORGANISM: Human endogenous retrovirus

<400> SEQUENCE: 47

Gly Lys Pro Cys Pro Lys Glu Ile Pro Lys Glu Ser Lys Asn Thr Glu
1               5                   10                  15
Val

<210> SEQ ID NO 48
<211> LENGTH: 17
<212> TYPE: PRT
<213> ORGANISM: Human endogenous retrovirus -continued
<210> SEQ ID NO 48
<211> LENGTH: 17
<212> TYPE: PRT
<213> ORGANISM: Human endogenous retrovirus

<400> SEQUENCE: 48

Lys Pro Cys Pro Lys Glu Ile Pro Lys Glu Ser Lys Asn Thr Glu Val
1               5                   10                  15
Leu

<210> SEQ ID NO 49
<211> LENGTH: 17
<212> TYPE: PRT
<213> ORGANISM: Human endogenous retrovirus

<400> SEQUENCE: 49

Pro Cys Pro Lys Glu Ile Pro Lys Glu Ser Lys Asn Thr Glu Val Leu
1               5                   10                  15
Val

<210> SEQ ID NO 50
<211> LENGTH: 17
<212> TYPE: PRT
<213> ORGANISM: Human endogenous retrovirus

<400> SEQUENCE: 50

Cys Pro Lys Glu Ile Pro Lys Glu Ser Lys Asn Thr Glu Val Leu Val
1               5                   10                  15
Trp

<210> SEQ ID NO 51
<211> LENGTH: 17
<212> TYPE: PRT
<213> ORGANISM: Human endogenous retrovirus

<400> SEQUENCE: 51

Pro Lys Glu Ile Pro Lys Glu Ser Lys Asn Thr Glu Val Leu Val Trp
1               5                   10                  15
Glu

<210> SEQ ID NO 52
<211> LENGTH: 20
<212> TYPE: PRT
<213> ORGANISM: Human endogenous retrovirus

<400> SEQUENCE: 52

Ser Tyr Gln Arg Ser Leu Lys Phe Arg Pro Lys Gly Lys Pro Cys Pro
1               5                   10                  15
Lys Glu Ile Pro
            20

<210> SEQ ID NO 53
<211> LENGTH: 5
<212> TYPE: RNA
<213> ORGANISM: artificial sequence
<220> FEATURE:
<223> OTHER INFORMATION: Stop-start cassette

<400> SEQUENCE: 53 uaaug                                                           5

<210> SEQ ID NO 54
<211> LENGTH: 10
<212> TYPE: RNA
<213> ORGANISM: artificial sequence
<220> FEATURE:

-continued

```
<223> OTHER INFORMATION: Kozak Sequence

<400> SEQUENCE: 54 ccrgccaugg                                                              10

<210> SEQ ID NO 55
<211> LENGTH: 11
<212> TYPE: DNA
<213> ORGANISM: Influenza A virus

<400> SEQUENCE: 55
caggtagatt g                                                            11

<210> SEQ ID NO 56
<211> LENGTH: 11
<212> TYPE: DNA
<213> ORGANISM: artificial sequence
<220> FEATURE:
<223> OTHER INFORMATION: U5 snRNA complementary strand

<400> SEQUENCE: 56
caggtaagta t                                                            11

<210> SEQ ID NO 57
<211> LENGTH: 32
<212> TYPE: DNA
<213> ORGANISM: artificial sequence
<220> FEATURE:
<223> OTHER INFORMATION: lariat consensus sequence

<400> SEQUENCE: 57
tactaacctt cttctctttc ttctcctgac ag                                     32

<210> SEQ ID NO 58
<211> LENGTH: 14
<212> TYPE: PRT
<213> ORGANISM: mouse

<400> SEQUENCE: 58

Leu Leu Trp Val Leu Leu Leu Trp Val Pro Gly Ser Thr Gly
1               5                   10

<210> SEQ ID NO 59
<211> LENGTH: 21
<212> TYPE: PRT
<213> ORGANISM: Influenza A virus

<400> SEQUENCE: 59

Met Asp Pro Asn Thr Val Ser Ser Phe Gln Val Ser Ile Phe Leu Trp
1               5                   10                  15

Arg Val Arg Lys Arg
            20

<210> SEQ ID NO 60
<211> LENGTH: 160
<212> TYPE: PRT
<213> ORGANISM: human

<400> SEQUENCE: 60

Met Asp Pro Asn Thr Val Ser Ser Phe Gln Val Ser Leu Leu Leu Trp
1               5                   10                  15

Val Leu Leu Leu Trp Val Pro Gly Ser Thr Gly Ala Pro Thr Ser Ser
            20                  25                  30
```

```
Ser Thr Lys Lys Thr Gln Leu Gln Leu Glu His Leu Leu Leu Asp Leu
        35                  40                  45

Gln Met Ile Leu Asn Gly Ile Asn Asn Tyr Lys Asn Pro Lys Leu Thr
    50                  55                  60

Arg Met Leu Thr Phe Lys Phe Tyr Met Pro Lys Lys Ala Thr Glu Leu
65                  70                  75                  80

Lys His Leu Gln Cys Leu Glu Glu Glu Leu Lys Pro Leu Glu Glu Val
                85                  90                  95

Leu Asn Leu Ala Gln Ser Lys Asn Phe His Leu Arg Pro Arg Asp Leu
                100                 105                 110

Ile Ser Asn Ile Asn Val Ile Val Leu Glu Leu Lys Gly Ser Glu Thr
                115                 120                 125

Thr Phe Met Cys Glu Tyr Ala Asp Glu Thr Ala Thr Ile Val Glu Phe
                130                 135                 140

Leu Asn Arg Trp Ile Thr Phe Cys Gln Ser Ile Ile Ser Thr Leu Thr
145                 150                 155                 160

<210> SEQ ID NO 61
<211> LENGTH: 21
<212> TYPE: PRT
<213> ORGANISM: Influenza A virus

<400> SEQUENCE: 61

Met Asp Pro Asn Thr Val Ser Ser Phe Gln Val Asp Cys Phe Leu Trp
1               5                   10                  15

Arg Val Arg Lys Arg
            20

<210> SEQ ID NO 62
<211> LENGTH: 160
<212> TYPE: PRT
<213> ORGANISM: artificial sequence
<220> FEATURE:
<223> OTHER INFORMATION: NS1-IgKappa-IL2 construct

<400> SEQUENCE: 62

Met Asp Pro Asn Thr Val Ser Ser Phe Gln Val Phe Ala Leu Leu Trp
1               5                   10                  15

Val Leu Leu Leu Trp Val Pro Gly Ser Thr Gly Ala Pro Thr Ser Ser
            20                  25                  30

Ser Thr Lys Lys Thr Gln Leu Gln Leu Glu His Leu Leu Leu Asp Leu
        35                  40                  45

Gln Met Ile Leu Asn Gly Ile Asn Asn Tyr Lys Asn Pro Lys Leu Thr
    50                  55                  60

Arg Met Leu Thr Phe Lys Phe Tyr Met Pro Lys Lys Ala Thr Glu Leu
65                  70                  75                  80

Lys His Leu Gln Cys Leu Glu Glu Glu Leu Lys Pro Leu Glu Glu Val
                85                  90                  95

Leu Asn Leu Ala Gln Ser Lys Asn Phe His Leu Arg Pro Arg Asp Leu
                100                 105                 110

Ile Ser Asn Ile Asn Val Ile Val Leu Glu Leu Lys Gly Ser Glu Thr
                115                 120                 125

Thr Phe Met Cys Glu Tyr Ala Asp Glu Thr Ala Thr Ile Val Glu Phe
                130                 135                 140

Leu Asn Arg Trp Ile Thr Phe Cys Gln Ser Ile Ile Ser Thr Leu Thr
145                 150                 155                 160
```

<210> SEQ ID NO 63
<211> LENGTH: 15
<212> TYPE: DNA
<213> ORGANISM: artificial sequence
<220> FEATURE:
<223> OTHER INFORMATION: Kozak Sequence

<400> SEQUENCE: 63
taagccgcca ccatg                                                        15

<210> SEQ ID NO 64
<211> LENGTH: 154
<212> TYPE: PRT
<213> ORGANISM: artificial sequence
<220> FEATURE:
<223> OTHER INFORMATION: NS1-GMCSF-IgKappa construct

<400> SEQUENCE: 64

Met Asp Pro Asn Thr Val Ser Ser Phe Gln Val Phe Ala Leu Leu Trp
1               5                   10                  15

Val Leu Leu Leu Trp Val Pro Arg Ser His Gly Ala Pro Ala Arg Ser
            20                  25                  30

Pro Ser Pro Ser Thr Gln Pro Trp Glu His Val Asn Ala Ile Gln Glu
        35                  40                  45

Ala Arg Arg Leu Leu Asn Leu Ser Arg Asp Thr Ala Ala Glu Met Asn
    50                  55                  60

Glu Thr Val Glu Val Ile Ser Glu Met Phe Asp Leu Gln Glu Pro Thr
65                  70                  75                  80

Cys Leu Gln Thr Arg Leu Glu Leu Tyr Lys Gln Gly Leu Arg Gly Ser
                85                  90                  95

Leu Thr Lys Leu Lys Gly Pro Leu Thr Met Met Ala Ser His Tyr Lys
            100                 105                 110

Gln His Cys Pro Pro Thr Pro Glu Thr Ser Cys Ala Thr Gln Ile Ile
        115                 120                 125

Thr Phe Glu Ser Phe Lys Glu Asn Leu Lys Asp Phe Leu Leu Val Ile
    130                 135                 140

Pro Phe Asp Cys Trp Glu Pro Val Gln Glu
145                 150

<210> SEQ ID NO 65
<211> LENGTH: 97
<212> TYPE: PRT
<213> ORGANISM: artificial sequence
<220> FEATURE:
<223> OTHER INFORMATION: CCL-3 NS1-IgKappa construct

<400> SEQUENCE: 65

Met Asp Pro Asn Thr Val Ser Ser Phe Gln Val Phe Ala Leu Leu Trp
1               5                   10                  15

Val Leu Leu Leu Trp Val Pro Arg Ser His Gly Ala Pro Leu Ala Ala
            20                  25                  30

Asp Thr Pro Thr Ala Cys Cys Phe Ser Tyr Thr Ser Arg Gln Ile Pro
        35                  40                  45

Gln Asn Phe Ile Ala Asp Tyr Phe Glu Thr Ser Ser Gln Cys Ser Lys
    50                  55                  60

Pro Ser Val Ile Phe Leu Thr Lys Arg Gly Arg Gln Val Cys Ala Asp
65                  70                  75                  80

Pro Ser Glu Glu Trp Val Gln Lys Tyr Val Ser Asp Leu Glu Leu Ser
                85                  90                  95

Ala

<210> SEQ ID NO 66
<211> LENGTH: 97
<212> TYPE: PRT
<213> ORGANISM: artificial sequence
<220> FEATURE:
<223> OTHER INFORMATION: CCL-20-NS1IgKappa construct

<400> SEQUENCE: 66

```
Met Asp Pro Asn Thr Val Ser Ser Phe Gln Val Phe Ala Leu Leu Trp
1               5                   10                  15
Val Leu Leu Leu Trp Val Pro Arg Ser His Gly Ala Ser Asn Phe Asp
                20                  25                  30
Cys Cys Leu Gly Tyr Thr Asp Arg Ile Leu His Pro Lys Phe Ile Val
            35                  40                  45
Gly Phe Thr Arg Gln Leu Ala Asn Glu Gly Cys Asp Ile Asn Ala Ile
        50                  55                  60
Ile Phe His Thr Lys Lys Lys Leu Ser Val Cys Ala Asn Pro Lys Gln
65                  70                  75                  80
Thr Trp Val Lys Tyr Ile Val Arg Leu Leu Ser Lys Lys Val Lys Asn
                85                  90                  95
Met
```

<210> SEQ ID NO 67
<211> LENGTH: 807
<212> TYPE: DNA
<213> ORGANISM: Mycobacterium tuberculosis

<400> SEQUENCE: 67

```
agcaaaagca gggtgacaaa gacataatgg atccaaacac tgtgtcaagc tttcaggtat    60
ttgccctgct ctgggtgctg ctgctgtggg tgccccggtc ccacggcatg accgagcagc   120
agtggaactt cgccggcatc gaggccgccg ctagcgccat ccagggcaac gtgaccagca   180
tccacagcct gctggacgag ggcaagcaga gcctgaccaa gctggcagct gcctggggcg   240
gctctggcag cgaggcctac cagggcgtgc agcagaagtg ggacgccacc gccaccgagc   300
tgaacaacgc cctgcagaac ctggcccgga ccatcagcga ggccggacag gccatggcca   360
gcaccgaggg caatgtgaca ggcatgttcg cctgatgacc aagcagaaag tggtactaac   420
cttcttctct ttcttctcct gacaggacat actgctgagg atgtcaaaaa tgcagttgga   480
gtcctcatcg ggggacttga atggaatgat aacacagttc gagtctctga aactctacag   540
agattcgctt ggagaagcag taatgagaat gggagacctc cactcactcc aaaacagaaa   600
cgagaaatgg cgggaacaat taggtcagaa gtttgaagaa ataagatggt tgattgaaga   660
agtgagacac aaaactgaaga taacagagaa tagttttgag caaataacat ttatgcaagc   720
cttacatcta ttgcttgaag tggagcaaga gataagaact ttctcgtttc agcttattta   780
ataataaaaa acacccttgt ttctact                                       807
```

<210> SEQ ID NO 68
<211> LENGTH: 765
<212> TYPE: DNA
<213> ORGANISM: Mycobacterium tuberculosis

<400> SEQUENCE: 68

```
agcaaaagca gggtgacaaa gacataatgg atccaaacac tgtgtcaagc tttcaggtat    60
ttgccatgac cgagcagcag tggaacttcg ccggcatcga ggccgcagcc agcgccatcc   120
```

```
agggcaacgt gaccagcatc cacagcctgc tggacgaggg caagcagagc ctgaccaagc    180
tggccgcagc ctggggcggc tctggcagcg aggcctacca gggcgtgcag cagaagtggg    240
acgccaccgc caccgagctg aacaacgccc tgcagaacct ggcccggacc atcagcgagg    300
ccggacaggc catggccagc accgagggca atgtgacagg catgttcgcc tgatgaccaa    360
gcagaaagtg gtactaacct tcttctcttt cttctcctga caggacatac tgctgaggat    420
gtcaaaaatg cagttggagt cctcatcggg ggacttgaat ggaatgataa cacagttcga    480
gtctctgaaa ctctacagag attcgcttgg agaagcagta atgagaatgg gagacctcca    540
ctcactccaa aacagaaacg agaaatggcg ggaacaatta ggtcagaagt ttgaagaaat    600
aagatggttg attgaagaag tgagacacaa actgaagata acagagaata gttttgagca    660
aataacattt atgcaagcct tacatctatt gcttgaagtg gagcaagaga taagaacttt    720
ctcgtttcag cttatttaat aataaaaaac acccttgttt ctact                    765
```

<210> SEQ ID NO 69
<211> LENGTH: 141
<212> TYPE: PRT
<213> ORGANISM: artificial sequence
<220> FEATURE:
<223> OTHER INFORMATION: IL-15 NS1 IgKappa construct

<400> SEQUENCE: 69

```
Met Asp Pro Asn Thr Val Ser Ser Phe Gln Val Phe Ala Leu Leu Trp
1               5                   10                  15

Val Leu Leu Leu Trp Val Pro Arg Ser His Gly Asn Trp Val Asn Val
            20                  25                  30

Ile Ser Asp Leu Lys Lys Ile Glu Asp Leu Ile Gln Ser Met His Ile
        35                  40                  45

Asp Ala Thr Leu Tyr Thr Glu Ser Asp Val His Pro Ser Cys Lys Val
    50                  55                  60

Thr Ala Met Lys Cys Phe Leu Leu Glu Leu Gln Val Ile Ser Leu Glu
65                  70                  75                  80

Ser Gly Asp Ala Ser Ile His Asp Thr Val Glu Asn Leu Ile Ile Leu
                85                  90                  95

Ala Asn Asn Ser Leu Ser Ser Asn Gly Asn Val Thr Glu Ser Gly Cys
            100                 105                 110

Lys Glu Cys Glu Glu Leu Glu Glu Lys Asn Ile Lys Glu Phe Leu Gln
        115                 120                 125

Ser Phe Val His Ile Val Gln Met Phe Ile Asn Thr Ser
    130                 135                 140
```

<210> SEQ ID NO 70
<211> LENGTH: 122
<212> TYPE: PRT
<213> ORGANISM: Mycobacterium tuberculosis

<400> SEQUENCE: 70

```
Met Asp Pro Asn Thr Val Ser Ser Phe Gln Val Phe Ala Leu Leu Trp
1               5                   10                  15

Val Leu Leu Leu Trp Val Pro Arg Ser His Gly Met Thr Glu Gln Gln
            20                  25                  30

Trp Asn Phe Ala Gly Ile Glu Ala Ala Ala Ser Ala Ile Gln Gly Asn
        35                  40                  45

Val Thr Ser Ile His Ser Leu Leu Asp Glu Gly Lys Gln Ser Leu Thr
    50                  55                  60
```

Lys Leu Ala Ala Ala Trp Gly Gly Ser Gly Ser Glu Ala Tyr Gln Gly
65                  70                  75                  80

Val Gln Gln Lys Trp Asp Ala Thr Ala Thr Glu Leu Asn Asn Ala Leu
            85                  90                  95

Gln Asn Leu Ala Arg Thr Ile Ser Glu Ala Gly Gln Ala Met Ala Ser
        100                 105                 110

Thr Glu Gly Asn Val Thr Gly Met Phe Ala
        115                 120

<210> SEQ ID NO 71
<211> LENGTH: 108
<212> TYPE: PRT
<213> ORGANISM: artificial
<220> FEATURE:
<223> OTHER INFORMATION: Fusion protein NS1 Mycobacterium tuberculosis
      ESAT6

<400> SEQUENCE: 71

Met Asp Pro Asn Thr Val Ser Ser Phe Gln Val Phe Ala Met Thr Glu
1               5                   10                  15

Gln Gln Trp Asn Phe Ala Gly Ile Glu Ala Ala Ala Ser Ala Ile Gln
            20                  25                  30

Gly Asn Val Thr Ser Ile His Ser Leu Leu Asp Glu Gly Lys Gln Ser
        35                  40                  45

Leu Thr Lys Leu Ala Ala Ala Trp Gly Gly Ser Gly Ser Glu Ala Tyr
    50                  55                  60

Gln Gly Val Gln Gln Lys Trp Asp Ala Thr Ala Thr Glu Leu Asn Asn
65                  70                  75                  80

Ala Leu Gln Asn Leu Ala Arg Thr Ile Ser Glu Ala Gly Gln Ala Met
            85                  90                  95

Ala Ser Thr Glu Gly Asn Val Thr Gly Met Phe Ala
        100                 105

<210> SEQ ID NO 72
<211> LENGTH: 17
<212> TYPE: PRT
<213> ORGANISM: artificial
<220> FEATURE:
<223> OTHER INFORMATION: synthetic signal peptide

<400> SEQUENCE: 72

Trp Val Leu Phe Ile Leu Leu Phe Leu Phe Leu Pro Arg Ser His
1               5                   10                  15

Gly

<210> SEQ ID NO 73
<211> LENGTH: 163
<212> TYPE: PRT
<213> ORGANISM: artificial
<220> FEATURE:
<223> OTHER INFORMATION: delNS1-IL2-21 segment

<400> SEQUENCE: 73

Met Asp Pro Asn Thr Val Ser Ser Phe Gln Val Phe Ala Trp Val Leu
1               5                   10                  15

Phe Ile Leu Leu Leu Phe Leu Phe Leu Pro Arg Ser His Gly Ala Pro
            20                  25                  30

Thr Ser Ser Ser Thr Lys Lys Thr Gln Leu Gln Leu Glu His Leu Leu
        35                  40                  45

```
Leu Asp Leu Gln Met Ile Leu Asn Gly Ile Asn Asn Tyr Lys Asn Pro
        50                  55                  60

Lys Leu Thr Arg Met Leu Thr Phe Lys Phe Tyr Met Pro Lys Lys Ala
 65                  70                  75                  80

Thr Glu Leu Lys His Leu Gln Cys Leu Glu Glu Glu Leu Lys Pro Leu
                 85                  90                  95

Glu Glu Val Leu Asn Leu Ala Gln Ser Lys Asn Phe His Leu Arg Pro
            100                 105                 110

Arg Asp Leu Ile Ser Asn Ile Asn Val Ile Val Leu Glu Leu Lys Gly
                115                 120                 125

Ser Glu Thr Thr Phe Met Cys Glu Tyr Ala Asp Glu Thr Ala Thr Ile
130                 135                 140

Val Glu Phe Leu Asn Arg Trp Ile Thr Phe Cys Gln Ser Ile Ile Ser
145                 150                 155                 160

Thr Leu Thr

<210> SEQ ID NO 74
<211> LENGTH: 18
<212> TYPE: PRT
<213> ORGANISM: human

<400> SEQUENCE: 74

Ala Gly Ala Ala Leu Leu Ala Leu Leu Ala Ala Leu Leu Pro Ala Ser
 1               5                  10                  15

Arg Ala

<210> SEQ ID NO 75
<211> LENGTH: 24
<212> TYPE: PRT
<213> ORGANISM: human

<400> SEQUENCE: 75

Met Arg Pro Ser Gly Thr Ala Gly Ala Ala Leu Leu Ala Leu Leu Ala
 1               5                  10                  15

Ala Leu Cys Pro Ala Ser Arg Ala
                 20

<210> SEQ ID NO 76
<211> LENGTH: 164
<212> TYPE: PRT
<213> ORGANISM: artificial
<220> FEATURE:
<223> OTHER INFORMATION: delNS1-IL2-24

<400> SEQUENCE: 76

Met Asp Pro Asn Thr Val Ser Ser Phe Gln Val Phe Ala Ala Gly Ala
 1               5                  10                  15

Ala Leu Leu Ala Leu Leu Ala Ala Leu Leu Pro Ala Ser Arg Ala Ala
             20                  25                  30

Pro Thr Ser Ser Ser Thr Lys Lys Thr Gln Leu Gln Leu Glu His Leu
             35                  40                  45

Leu Leu Asp Leu Gln Met Ile Leu Asn Gly Ile Asn Asn Tyr Lys Asn
         50                  55                  60

Pro Lys Leu Thr Arg Met Leu Thr Phe Lys Phe Tyr Met Pro Lys Lys
 65                  70                  75                  80

Ala Thr Glu Leu Lys His Leu Gln Cys Leu Glu Glu Glu Leu Lys Pro
                 85                  90                  95

Leu Glu Glu Val Leu Asn Leu Ala Gln Ser Lys Asn Phe His Leu Arg
```

```
                    100                 105                 110
Pro Arg Asp Leu Ile Ser Asn Ile Asn Val Ile Val Leu Glu Leu Lys
        115                 120                 125

Gly Ser Glu Thr Thr Phe Met Cys Glu Tyr Ala Asp Glu Thr Ala Thr
        130                 135                 140

Ile Val Glu Phe Leu Asn Arg Trp Ile Thr Phe Cys Gln Ser Ile Ile
145                 150                 155                 160

Ser Thr Leu Thr

<210> SEQ ID NO 77
<211> LENGTH: 1023
<212> TYPE: DNA
<213> ORGANISM: artificial
<220> FEATURE:
<223> OTHER INFORMATION: delta NS influenza B IL2 construct

<400> SEQUENCE: 77
agcagaagca gaggatttgt ttagtcactg gcaaacagga aaaaatggcg aacaacatga      60
ccacaacaca aattgaggtg ggtccgggag caaccaatgc caccataaac tttgaagcag     120
gaattctgga gtgctatgaa aggctttcat ggcaaagata atgtacagga tgcaactcct     180
gtcttgcatt gcactaagtc ttgcacttgt cacaaacagt gcacctactt cttcgtcgac     240
aaagaaaaca cagctacaac tggagcattt actgctggat ttacagatga ttttgaatgg     300
aattaataat tacaagaatc ccaaactcac caggatgctc acatttaagt tttacatgcc     360
caagaaggcc acagaactga acatcttca gtgtctagaa gaagaactca acctctggaa     420
ggaagtgcta aatttagctc aaagcaaaaa ctttcactta gacccagggg acttaatcag     480
caatatcaac gtaatagttc tggaactaaa gggatctgaa acaacattca tgtgtgaata     540
tgctgatgag acagcaacca ttgtagaatt tctgaacaga tggattacct tttgtcaaag     600
catcatctca acactaactt gataatacta accttcttct ctttcttctc ctgacagtgg     660
aggatgaaga agatggccat cggatcctca actcactctt cgagcgtctt aatgaaggac     720
attcaaagcc aattcgagca gctgaaactg cggtgggagt cttatcccaa tttggtcaag     780
agcaccgatt atcaccagaa gagggagaca attagactgg tcacggaaga actttatctt     840
ttaagtaaaa gaattgatga taacatatta ttccacaaaa cagtaatagc taacagctcc     900
ataatagctg acatggttgt atcattatca ttattgaaaa cattgtatga aatgaaggat     960
gtggttgaag tgtacagcag gcagtgcttg tgaatttaaa ataaaaatcc tcttgttact    1020
act                                                                   1023

<210> SEQ ID NO 78
<211> LENGTH: 930
<212> TYPE: DNA
<213> ORGANISM: artificial
<220> FEATURE:
<223> OTHER INFORMATION: delNS1-IL2-23 sequence

<400> SEQUENCE: 78
agcaaaagca gggtgacaaa acataatgg atccaaacac tgtgtcaagc tttcaggtat      60
ttgcctgggt gctttttcata cttctgcttt tcctgttcct tccaagatca catggtgcac     120
ctacttcttc gtcgacaaag aaaacacagc tacaactgga gcatttactg ctggatttac     180
agatgatttt gaatggaatt aataattaca agaatcccaa actcaccagg atgctcacat     240
ttaagtttta catgcccaag aaggccacag aactgaaaca tcttcagtgt ctagaagaag     300
```

-continued

```
aactcaaacc tctggaggaa gtgctaaatt tagctcaaag caaaaacttt cacttaagac    360
ccagggactt aatcagcaat atcaacgtaa tagttctgga actaaaggga tctgaaacaa    420
cattcatgtg tgaatatgct gatgagacag caaccattgt agaatttctg aacagatgga    480
ttaccttttg tcaaagcatc atctcaacac taacttgata accaagcaga aagtggtact    540
aaccttcttc tctttcttct cctgacagga catactgctg aggatgtcaa aaatgcagtt    600
ggagtcctca tcgggggact tgaatggaat gataacacag ttcgagtctc tgaaactcta    660
cagagattcg cttggagaag cagtaatgag aatgggagac ctccactcac tccaaaacag    720
aaacgagaaa tggcgggaac aattaggtca gaagtttgaa gaaataagat ggttgattga    780
agaagtgaga cacaaactga agataacaga gaatagtttt gagcaaataa catttatgca    840
agccttacat ctattgcttg aagtggagca agagataaga actttctcgt ttcagcttat    900
ttaataataa aaaacaccct tgtttctact                                      930
```

<210> SEQ ID NO 79
<211> LENGTH: 933
<212> TYPE: DNA
<213> ORGANISM: artificial
<220> FEATURE:
<223> OTHER INFORMATION: delNS1-IL2-24 sequence

<400> SEQUENCE: 79

```
agcaaaagca gggtgacaaa aacataatgg atccaaacac tgtgtcaagc tttcaggtat     60
ttgccgcagg agctgcactt ttggcacttc ttgctgcact tcttcctgct tcaagagctg    120
cacctacttc ttcgtcgaca aagaaaacac agctacaact ggagcattta ctgctggatt    180
tacagatgat tttgaatgga attaataatt acaagaatcc caaactcacc aggatgctca    240
catttaagtt ttacatgccc aagaaggcca cagaactgaa acatcttcag tgtctagaag    300
aagaactcaa acctctggag gaagtgctaa atttagctca aagcaaaaac tttcacttaa    360
gacccaggga cttaatcagc aatatcaacg taatagttct ggaactaaag ggatctgaaa    420
caacattcat gtgtgaatat gctgatgaga cagcaaccat tgtagaattt ctgaacagat    480
ggattacctt ttgtcaaagc atcatctcaa cactaacttg ataaccaagc agaaagtggt    540
actaaccttc ttctctttct tctcctgaca ggacatactg ctgaggatgt caaaaatgca    600
gttggagtcc tcatcggggg acttgaatgg aatgataaca cagttcgagt ctctgaaact    660
ctacagagat tcgcttggag aagcagtaat gagaatggga gacctccact cactccaaaa    720
cagaaacgag aaatggcggg aacaattagg tcagaagttt gaagaaataa gatggttgat    780
tgaagaagtg agacacaaac tgaagataac agagaatagt tttgagcaaa taacatttat    840
gcaagcctta catctattgc ttgaagtgga gcaagagata agaactttct cgtttcagct    900
tatttaataa taaaaaacac ccttgtttct act                                  933
```

<210> SEQ ID NO 80
<211> LENGTH: 230
<212> TYPE: PRT
<213> ORGANISM: Influenza A virus

<400> SEQUENCE: 80

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
```

```
                35                  40                  45
Thr Leu Gly Leu Asp Ile Glu Thr Ala Thr Arg Ala Gly Lys Gln Ile
        50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Arg Met Asp Gln Ala Ile Met Asp Lys Asn Ile
            115                 120                 125

Ile Leu Lys Ala Asn Phe Ser Val Ile Phe Asp Arg Leu Glu Thr Leu
        130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
            195                 200                 205

Asn Gly Arg Pro Pro Leu Thr Pro Lys Gln Lys Arg Glu Met Ala Gly
        210                 215                 220

Thr Ile Arg Ser Glu Val
225                 230

<210> SEQ ID NO 81
<211> LENGTH: 5
<212> TYPE: DNA
<213> ORGANISM: artificial
<220> FEATURE:
<223> OTHER INFORMATION: stop/start codon

<400> SEQUENCE: 81 taatg                                                               5

<210> SEQ ID NO 82
<211> LENGTH: 20
<212> TYPE: PRT
<213> ORGANISM: artificial
<220> FEATURE:
<223> OTHER INFORMATION: modified Ig Kappa signal sequence

<400> SEQUENCE: 82

Met Glu Thr Asp Thr Leu Leu Leu Trp Val Leu Leu Leu Trp Val Pro
1               5                   10                  15

Arg Ser His Gly
            20
```

REPLICATION DEFICIENT INFLUENZA VIRUS FOR THE EXPRESSION OF HETEROLOGOUS SEQUENCES

CROSS-REFERENCE TO RELATED APPLICATIONS

This application is a continuation of U.S. patent application Ser. No. 12/666,246, filed on Dec. 22, 2009 and entitled REPLICATION DEFICIENT INFLUENZA VIRUS FOR THE EXPRESSION OF HETEROLOGOUS SEQUENCES, which was the U.S. national stage of International Patent Application No. PCT/EP2008/058154, filed on Jun. 26, 2008 and entitled REPLICATION DEFICIENT INFLUENZA VIRUS FOR THE EXPRESSION OF HETEROLOGOUS SEQUENCES, which claims the benefit of priority under 35 U.S.C. §120 from U.S. Patent Application No. 60/946,644, filed on Jun. 27, 2007 and entitled NOVEL VIRAL VECTOR FOR THE EXPRESSION OF HETEROLOGOUS SEQUENCES, and under 35 U.S.C. §119 from European Patent Application No. 07450176.8, filed on Oct. 5, 2007 and entitled NOVEL VIRAL VECTOR FOR THE EXPRESSION OF HETEROLOGOUS SEQUENCES. The disclosures of the foregoing applications are incorporated herein by reference in their entirety.

SEQUENCE LISTING

The entire content of a Sequence Listing titled "Sequence_Listing.txt," created on Oct. 8, 2013 and having a size of 47 kilobytes, which has been submitted in electronic form in connection with the present application, is hereby incorporated by reference herein in its entirety.

FIELD OF THE INVENTION

The present invention covers a replication deficient influenza virus comprising a modified NS1 segment coding for an NS1 protein lacking a functional RNA binding domain and functional effector domain and a heterologous sequence inserted between the splice donor site and the splice acceptor site of the NS segment. Said heterologous sequence can be expressed either from the NS1 open reading frame or an open reading frame different from the NS1 open reading frame.

Further therapeutic preparations containing said replication deficient influenza virus and their use are covered as well as the process for manufacturing said virus.

The influenza virions consist of an internal ribonucleoprotein core (a helical nucleocapsid) containing the single-stranded RNA genome, and an outer lipoprotein envelope lined inside by a matrix protein (M1). The segmented genome of influenza A and B virus consists of eight molecules (seven for influenza C) of linear, negative polarity, single-stranded RNAs which encodes eleven (some influenza A strains ten) polypeptides, including: the RNA-dependent RNA polymerase proteins (PB2, PB1 and PA) and nucleoprotein (NP) which form the nucleocapsid; the matrix membrane proteins (M1, M2 or BM2 for influenza B, respectively); two surface glycoproteins which project from the lipid containing envelope: hemagglutinin (HA) and neuraminidase (NA); the non-structural protein (NS1) and the nuclear export protein (NEP). Influenza B viruses encode also NB, a membrane protein which might have ion channel activity and most influenza A strains also encode an eleventh protein (PB1-F2) believed to have proapoptotic properties.

Transcription and replication of the genome takes place in the nucleus and assembly occurs via budding on the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed and processed by a unique mechanism in which viral endonuclease cleaves the capped 5'-terminus from cellular heterologous mRNAs which then serve as primers for transcription from viral RNA templates by the viral transcriptase. Transcripts terminate at sites 15 to 22 bases from the ends of their templates, where oligo(U) sequences act as signals for the addition of poly(A) tracts. Of the eight viral RNA molecules of influenza A virus so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In most of influenza A viruses, segment 2 also encodes for a second protein (PB1-F2), expressed from an overlapping reading frame. In other words, the eight viral RNA segments code for eleven proteins: nine structural and 2 nonstructural (NS1 and the recently identified PB1-F2) proteins.

The application of viral vectors for delivery of foreign proteins and biologically active molecules is an attractive approach for gene therapy, treatment of cancer and prevention of infectious diseases. Influenza viruses are especially considered as potential vaccine vectors. In contrast to other vectors such as adenoviruses or retroviruses, influenza does not contain a DNA intermediate and is therefore not able to integrate into the host's chromosomes. There are several options to manipulate the influenza genome depending on the desired aims and possibilities to produce recombinant viruses. These strategies include the insertion of foreign proteins into the surface glycoproteins NA and HA (Muster T. et al., 1994, J. Virol., 68, 4031-4034; Percy N. et al., 1994, J. Virol., 68, 4486-4492), the creation of additional genomic fragments (Flick R and Hobom G., 1999, Virology, 262, 93-103; Watanabe T. et al., 2003, J. Virol., 77, 10575-10583) and the manipulation of the non-structural NS1 protein (Ferko B. et al., 2001, J. Virol., 8899-8908; Takasuka N. et al., 2002, Vaccine, 20, 1579-1585). The influenza NS1 protein has several advantages as a target for engineering since it does not presumably interfere with the structure of the virions, but is synthesized in large quantities in infected cells and tolerates long insertions up to several hundred nucleotides.

As NS1 is only expressed intracellulary and less exposed to the humoral arm of the immune system, the development of the immune response to the NS1 protein or to the proteins fused to NS1 is limited mainly to the induction of CD8$^+$ T cell immunity. Obviously, for the induction of B-cell response or for the expression of biologically active molecules, efficient delivery of the recombinant protein to the cell surface is required.

Vaccination is presently seen as the best way to protect humans against influenza. Annual human influenza epidemics (caused by influenza type A or type B viruses) are manifested as highly infectious acute respiratory disease with high morbidity and significant mortality. Vaccination is accomplished with commercially available, chemically inactivated (killed) or live attenuated influenza virus vaccines. The concept of the current live attenuated vaccine is based on the generation of a temperature sensitive attenuated "master strain" adapted to grow at 25° C. (cold adaptation). Live cold adapted (ca) and inactivated virus vaccine stimulate the immune system differently, yet in both cases lack of sufficient immunogenicity especially in elderly persons is one of the most important drawbacks in influenza vaccination. Although ca live influenza virus vaccines are considered as sufficiently safe, the exact genetic and molecular mechanisms of attenuation are not completely understood. It is claimed that the nature of the safety of ca influenza vaccines is based on a large number of point mutations distributed across the internal gene segments. However, only a small number of mapped mutations localized in the polymerase genes are responsible for the attenuation of ca virus strains that are unable to replicate at normal body temperature (Herlocher, M. L., A. C. Clavo, and H. F. Maassab. 1996, Virus Res. 42:11-25; Herlocher, M. L., H. F. et al., 1993, Proc Natl Acad Sci USA. 90:6032-6036). In fact, the genetic stability of live vaccine strains are often questioned since viruses re-isolated from vaccinated hosts reveal additional point mutations which might eventually function as "suppressor" mutations causing enhanced replication properties and a possible loss of the temperature sensitive phenotype of the revertant virus (Herlocher, M. L., H. F. et al., 1993, Proc. Natl. Acad. Sci. 90:6032-6036, Treanor, J., M. et al., 1994 J Virol. 68:7684-7688.)

Reflecting the potential risks of the ca live attenuated influenza virus vaccines and in view of the low stability often combined with low expression rate of foreign proteins in influenza virus vectors, there is still a high demand to create a completely attenuated influenza virus vector inducing cellular and/or humoral immunogenicity and stably expressing high amounts of foreign proteins.

It has been surprisingly shown by the inventors that an influenza virus vector as developed according to the invention does fulfill these unmet demands, i.e. providing an influenza virus vector that is of high safety due to complete attenuation and which shows stable expression of foreign genes inserted into the virus vector. Preferably, the foreign genes show high expression rates when inserted into the inventive virus vector.

Although various attempts have been made to overcome the issues of low genetic stability and low expression rate of proteins or peptides in attenuated virus vectors, none of these constructs have been efficiently successful yet.

Kittel et al. (Virology, 2004, 324, 67-73) described an influenza A virus consisting of an NS1 protein of 125 aa length (approx. one half of the wt NS1 protein) and expressing green fluorescent protein (GFP) from the NS1 reading frame, which was replicating in PKR knock out mice. In interferon competent cells the virus was not stably expressing GFP but the virus was loosing its fluorescent activity due to the appearance of various deletions within the GFP sequence.

A bicistronic expression strategy based on the insertion of an overlapping stop-start codon cassette into the NS gene for expressing GFP was disclosed by Kittel et al. (2005, J. Virol., 79, 10672-10677). Although being genetically stable, the expression level of the GFP from this reading frame was significantly lower than that obtained from an influenza virus vector expressing GFP from the NS1 ORF (Kittel et al., 2004, see above).

Ferko et al. did not describe a replication deficient virus but a ca influenza virus expressing human interleukin 2 (J. Virol., 2006, 11621-11627). Yet, the genetic stability and safety of a cold adapted virus has to be questioned in view of the genetic structure leading to temperature sensitivity (Herlocher M. et al., Proc. Natl. Acad. Sci, 1993, 90, 6032-6036). Additionally, the IL-2 expression levels were low.

The present invention relates to the development of a replication deficient influenza virus comprising a modified NS segment coding for an NS1 protein lacking a functional RNA binding domain and functional effector domain and a heterologous sequence inserted between the splice donor site and the splice acceptor site of the NS1 gene segment. According to the invention the heterologous sequence can be expressed from the NS1 reading frame or from a separate open reading frame.

Although WO 07/016,715 describes that influenza virus wherein the NS gene (sometimes referred to also as NS1 gene) comprises deletions and wherein the virus can be used to express an immunostimulatory cytokine, there is no disclosure on the specific influenza vector which could successfully express foreign proteins. In contrast, the inventors have surprisingly shown that the heterologous sequences, which can be even larger than the natural intron, can be stably expressed at high levels from the NS segment if inserted between a functional splice donor site and functional splice acceptor site, provided NS splicing efficiency is adjusted according to insert size.

This was neither shown nor indicated in WO 06/088481 and WO 01/64680.

According to a preferred embodiment of the invention, the functional splice donor site and the splice acceptor site of the NS gene segment is the natural splice site.

According to the invention the heterologous sequences can be selected from any biologically active proteins or peptides or antigenic structures.

Antigenic peptides or proteins are characterized by comprising epitopes which can lead to immunomodulatory activities, like binding of antibodies or antibody like structures or induction of cellular immune responses.

Preferably, proteins or peptides are selected from the group consisting of antigens, preferably bacterial antigens like ESAT6, growth factors, cytokines like interleukins, lymphokines and chemokines and fragments or derivatives thereof, more preferred from Mycobacterium tuberculosis, GM-CSF, CCL-3, CCL-20, interleukin 2, interleukin 15 or a fragment or derivative thereof.

The present invention further relates to therapeutic preparations, preferably vaccine preparations containing said replication deficient influenza viruses. Exemplarily these preparations can be used for the prevention and treatment of infectious diseases or cancer.

Further, methods for producing the inventive influenza viruses by transfecting cell lines (e.g. Vero cells, MDCK cells etc.) and expressing viral particles are disclosed.

FIGURES

FIG. 1 (*a-j*): Nucleic acid sequence of various vector constructs.

a: Sequence of the deINS1-IL-2-10 segment (SEQ ID No. 1)
b: Sequence of the deINS1-IL-2-11 segment (SEQ ID No. 2)
c: Sequence of the deINS1-IL-2-14 segment (SEQ ID No. 3)
d: Sequence of deINS1-IL2-13 segment (SEQ ID No. 4)
e: Sequence of deINS1-IL-2-21 segment (SEQ ID No. 5)
f: Sequence of deINS1-IL-2-17 segment (SEQ ID No. 6),
g: Sequence of deINS1-IL-15-21 segment (SEQ ID No. 7)
h: Sequence of deINS1-GM-CSF-21 segment (SEQ ID No. 8)
i: Sequence of deINS1-CCL-3-21 segment (SEQ ID No. 9)
j: Sequence of deINS1-CCL20-21 segment (SEQ ID No. 10)

k: Sequence of deINS1-ESAT-6s-21 segment (SEQ ID No. 67)

l: Sequence of deINS1-ESAT-6i-21 segment (SEQ ID No. 68)

m: Sequence of deINS1-IL2-23 segment (SEQ ID No. 78)

n: Sequence of deINS1-IL2-24 segment (SEQ ID No. 79)

FIG. 2: Schematic representation of the influenza A wild-type NS segment and the three chimeric IL-2 NS segments deINS1-IL-2-10 and deINS1-IL-2-11 and deINS1-IL-2-14.

Figure 3:
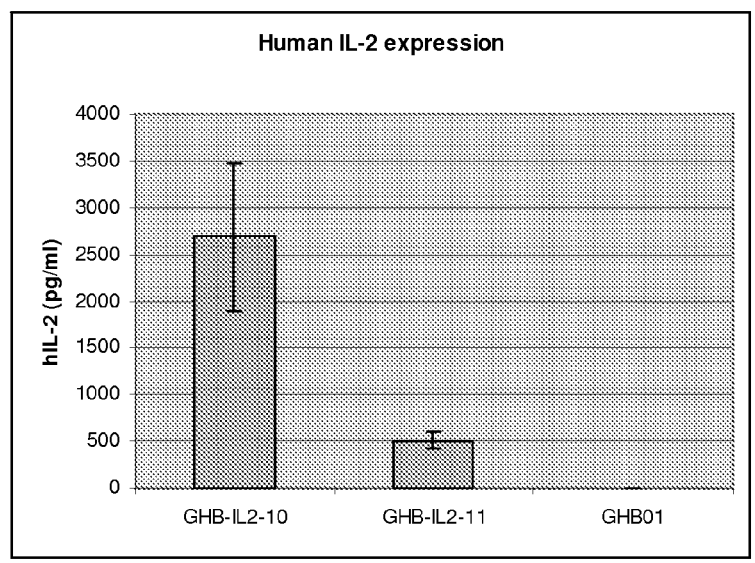

FIG. 3: Human IL-2 levels in supernatants from Vero cells infected with GHB-IL-2-10, GHB-IL-2-11 or GHB01.

Figure 4:
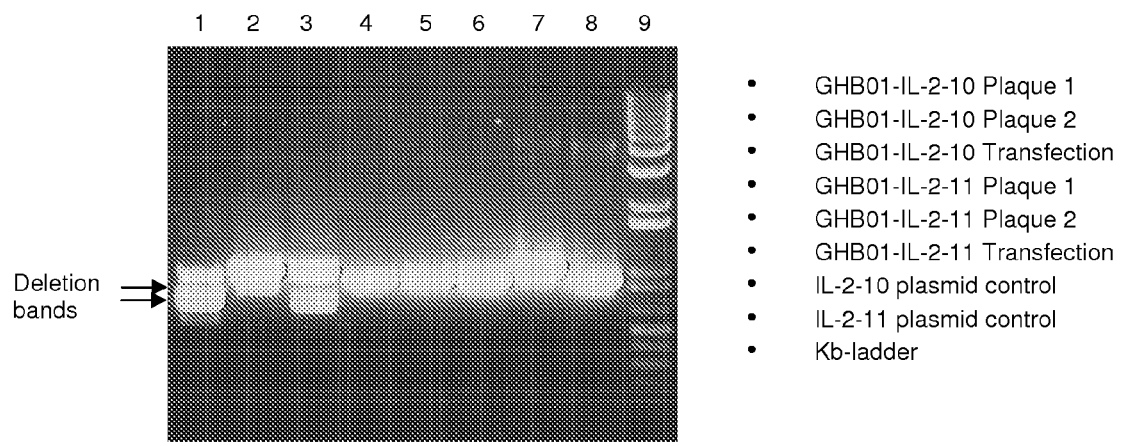

FIG. 4: RT-PCR analysis of the NS segment after five passages on Vero cells

Figure 5:
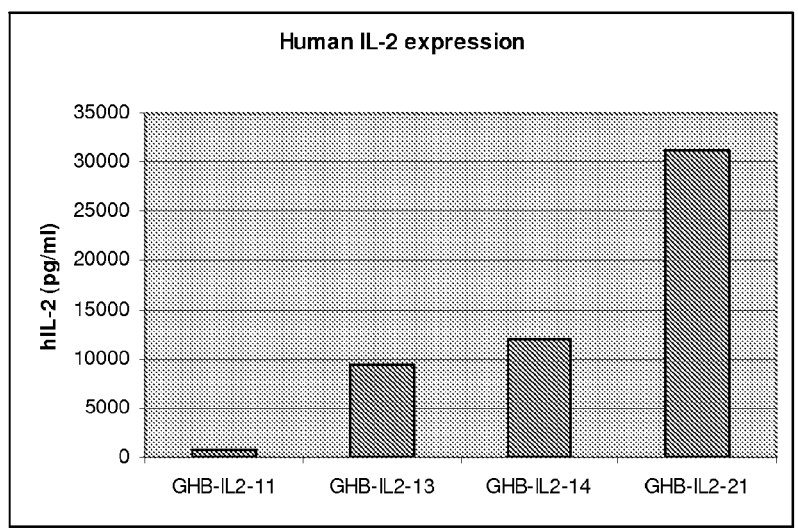

FIG. 5: Human IL-2 levels in supernatants from Vero cells infected with GHB-IL-2-11, GHB-IL-2-13, GHB-IL2-14 and GHB-IL2-21.

FIG. 6: Amino acid sequence of wt influenza virus PR8 NS1

Figure 7:
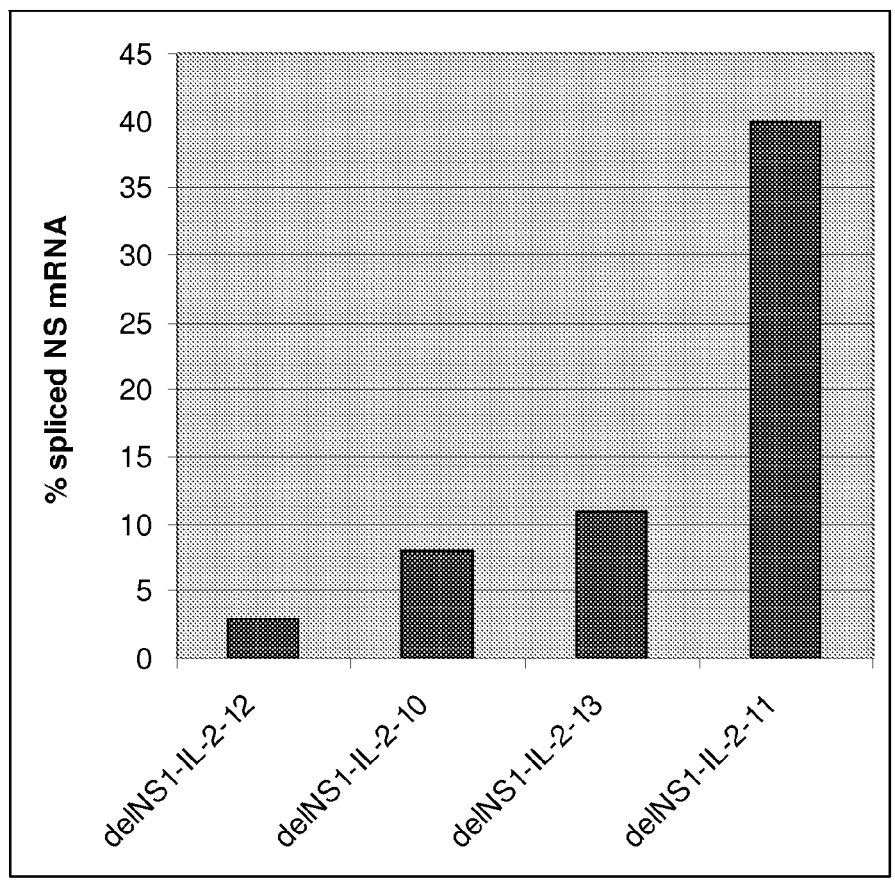

FIG. 7: deINS1-IL-2 mRNA splicing can be altered by either modifying the sequence surrounding the splice donor site or the sequences 5' to the splice acceptor site.

Figure 8:
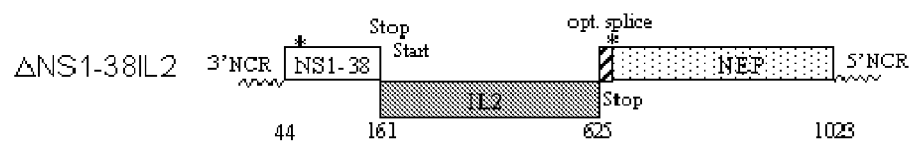

FIG. 8: Schematic IL-2 expression construct. The ORF of the truncated NS1 consists of nucleotides 45-158; the human IL-2 ORF consists of nucleotides 161-619; the 5' intron boundary is between nucleotides 77 and 78; the 3' intron boundary is between nucleotides 657 and 658.

FIG. 9: Nucleotide sequence of ΔNS1-38IL2 (SEQ ID No. 77).

The invention provides replication-deficient influenza viruses comprising a modified NS segment coding for a NS1 protein comprising at least one amino acid modification within positions 1 to 73 resulting in complete lack of its functional RNA binding and at least one amino acid between position 74 and the carboxy-terminal amino acid residue, specifically until amino acid position 167, resulting in complete lack of its effector function and a heterologous sequence between a functional splice donor site and functional splice acceptor site inserted in the NS gene segment.

Preferably the influenza virus is derived from influenza A virus, influenza B virus or influenza C virus. Vectors based on or derived from Influenza A or influenza B virus sequences are preferred.

The replication deficient influenza virus according to the invention can be used as viral vector for immunization against any pathogens or antigenic structures to induce an immune response against the heterologous structures expressed by said viral vector. The immune response can comprise a cellular immune response and/or a humoral immune response. By using heterologous sequences expressing immunomodulating proteins or peptides, the immune response towards the influenza virus can be further boosted, resulting in an improved influenza vaccine formulation. This is especially relevant for vaccination of elderly or immunosuppressed individuals.

The virus selected for use in the invention comprises a modified NS gene leading to an influenza virus that is attenuated, i.e. it is infectious and can replicate in vivo in interferon deficient cells or cell systems but does not replicate in interferon competent cells. According to the invention the term "replication deficient" is defined as replication rate in interferon competent host cells that is at least less than 5%, preferably less than 1%, preferably less than 0.1% than wild type influenza virus as determined by hemagglutination assay, TCID50 assay or plaque assay as well known in the art.

The NS gene segment according to the invention must contain functional splice donor and splice acceptor sites.

According to a specific embodiment of the invention, the influenza gene segments can be derived from different influenza strains, either pandemic or interpandemic ones. This can result in reassorted influenza viruses which combine the genes for the surface glycoproteins hemagglutinin (HA) and/or neuraminidase (NA) of actual interpandemic viruses with five or six or seven RNA segments coding for other proteins from the attenuated master strain (6/2 combination) or 7/1 reassortants or 5/3 reassortants containing HA, NA and M segments of a circulating strain respectively.

The inventors have used a reverse genetics system on Vero cells for developing reassortants and/or expression of modified influenza virus strains. The technology is already well known in the art (Pleschka S. et al., 1996, J. Virol., 70(6), 4188-4192, Neumann and Kawaoka, 1999, Adv. Virus Res., 53, 265-300, Hoffmann et al. 2000, Proc Natl Acad Sci USA. 97:6108-13). Alternatively, the technology based on RNPs as described by Enami and Enami (J. Virol, 2000, 74, 12, pp. 5556-5561) can be used for developing reassortants.

The NS1 protein of influenza A virus is a multifunctional protein that consists of approximately 230 amino acids and is early and abundantly synthesized in infection. It counters cellular antiviral activities and is a virulence factor. By the activity of its carboxy terminal region, the NS1 protein is able to inhibit the host m RNA's processing mechanisms. Second, it facilitates the preferential translation of viral mRNA by direct interaction with the cellular translation initiation factor. Third, by binding to dsRNA and interaction with putative cellular kinase(s), the NS1 protein is able to prevent the activation of interferon (IFN-) inducible dsRNA-activated kinase (PKR), 2'5'-oligoadenylate synthetase system and cytokine transcription factors. Fourth, the N terminal part of NS1 binds to RIG-I and inhibits downstream activation of IRF-3, preventing the transcriptional induction of IFN-β. Therefore the NS1 protein inhibits the expression of IFN-α or IFN-β genes, delays the development of apoptosis in the infected cells, and prevents the formation of the antiviral state in neighbouring cells. Influenza viruses containing modifications within the NS1 protein are known in the art. For example, WO 99/64571 describes the complete knock out of the NS gene segment, WO 99/64068 discloses various NS gene segments that have been partially deleted, yet none of the described modifications disclose an influenza virus vector according to the present invention.

According to the present invention the modification within the NS1 protein can be a deletion, an insertion or substitution of at least one amino acid resulting in a replication deficient influenza virus.

Preferably the modified NS1 protein comprises a deletion of at least 50% of the NS1 amino acids, preferably of at least 70%, more preferably of at least 90%. Alternatively, the functionality of the NS1 protein can be completely diminished.

The NS1 protein of the influenza virus vector according to the invention lacks the functional RNA binding domain. The primary function of this domain located at the amino end of the NS1 protein (amino acids 1-73, the wild type amino acid sequence is attached as SEQ ID No. 80) is binding dsRNA and inhibiting the 2'5' oligo (A) synthetase/RNase L pathway (Min J. et al., Proc. Natl. Acad. Sci, 2006, 103, 7100-7105, Chien et al., Biochemistry. 2004 Feb. 24; 43(7):1950-62) as well as the activation of a cytoplasmic RNA helicase, RIG-I, retinoic acid-inducible protein I (Yoneyama M. et al., Nat. Immunol., 2004, 5, 730-737).

Lack of a functional RNA binding domain is defined according to the present invention as complete lack of dsRNA binding ability leading to an influenza virus that does not replicate in interferon competent cells.

According to the invention the effector domain of the NS1 protein of influenza virus vector is not functional. The effector domain interacts with cellular proteins to inhibit mRNA nuclear export. The effector domain is located at the C-terminal part of the NS1 protein. According to Schultz et al. the effector domain is specifically located between amino acid residues 117 and 161, other literature locates the effector domain between 134 and 161. The NS1 effector domain can be completely or partially deleted as well as amino acids can be substituted or inserted and the remaining effector domain can be tested for functionality as described in the art (Schultz-Cherry S. et al., J. Virol., 2001, 7875-7881).

According to the invention the C-terminal amino acids relevant for effector binding activity are modified to inhibit effector function. Specifically amino acids at positions 74 to 230, more specifically amino acids at positions 116 to 161, more specifically at positions 134 to 161 are modified. According to a preferred embodiment, the modification is a deletion of said amino acids.

The heterologous sequence according to the present invention can be any biologically active protein or peptide or antigenic structure.

For example, antigenic structures can be proteins or carbohydrate structures which can be recognized by the immune system, e.g. antibodies or antibody-like structures can bind to these structures. These epitope structures can contain signal peptides or can be directly linked to the modified NS1 protein. For example, foreign epitope structures can be derived from other pathogens, from tumor associated antigens or retroviral epitopes expressed on the surface of tumour cells. Carbohydrate antigens are often of particularly weak immunogenicity. Their immunogenicity can be improved by conjugating the carbohydrate to a protein carrier. Proteins or peptides can also be linked to transmembrane domain sequences preferably containing stretches of hydrophobic amino acids or other leader sequences known to be needed for transporting the protein/peptide through the cellular membrane barriers. Transmembrane domain usually denotes a single transmembrane alpha helix of a transmembrane protein. An alpha-helix in a membrane can be folded independently from the rest of the protein, similar to domains of water-soluble proteins. A transmembrane domain can be any three-dimensional protein structure which is thermodynamically stable in a membrane. This may be a single alpha helix, a stable complex of several transmembrane alpha helices, a transmembrane beta barrel, a beta-helix of gramicidin A, or any other structure.

Transmembrane helices are usually about 20 amino acids in length, although they may be much longer or shorter.

For example these could be HA transmembrane sequences or any other known viral transmembrane domains.

The biologically active protein used according to the invention can comprise a signal peptide. The signal peptide can be any signal sequence being either a naturally occurring signal sequence or a synthetic one. For example it can be the naturally existing signal sequence of the heterologous sequence. Alternatively, it can also be derived from an antibody, preferably from an Ig kappa chain, more preferably from Ig kappa signal peptide. Preferably, the Ig kappa chain is derived from mouse Ig kappa chain.

According to a preferred embodiment of the invention the heterologous sequence expresses cytokines or chemokines or fragments or derivatives thereof. Cytokines are small secreted proteins which mediate and regulate immunity, inflammation and hematopoiesis. The largest group of cytokines are those which promote proliferation and differentiation of immune cells. Included within this group are interleukins, which are cytokines produced by leukocytes, and interferons, which may be produced by a variety of cell types.

Interferons (IFN) are a family of naturally occurring glycoproteins produced by cells of the immune system of vertebrates, including mammals, birds, reptiles and fish, in response to challenge by agents such as bacteria, viruses, parasites and tumour cells. In humans there are three major classes of interferons. The type I interferons include 14 IFN-alpha subtypes and single IFN-beta, omega, kappa and epsilon isoforms. Type II interferons consist of IFN-gamma and a recently discovered third class consists of IFN-lambda with three different isoforms.

Th1 cells secrete mainly IL-2, IFN-γ, and TNF-β, whereas Th2 cells which are relevant in humoral immune responses secrete cytokines such as IL-4, IL-5, and IL-10. Th2-type cytokines mediate delayed type hypersensitivity responses against intracellular pathogens and inhibit the Th1 responses.

Chemokines, originally derived from chemoattractant cytokines, actually comprise more than 50 members and represent a family of small, inducible, and secreted proteins of low molecular weight (6-12 kDa in their monomeric form) that play a decisive role during immunosurveillance and inflammatory processes. Depending on their function in immunity and inflammation, they can be distinguished into two classes. Inflammatory chemokines are produced by many different tissue cells as well as by immigrating leukocytes in response to bacterial toxins and inflammatory cytokines like IL-1, TNF and interferons. Their main function is to recruit leukocytes for host defense and in the process of inflammation. Homing chemokines, on the other hand, are expressed constitutively in defined areas of the lymphoid tissues. They direct the traffic and homing of lymphocytes and dendritic cells within the immune system. These chemokines, as illustrated by BCA-I, SDF-1 or SLC, control the relocation and recirculation of lymphocytes in the context of maturation, differentiation, activation and ensure their correct homing within secondary lymphoid organs.

According to the present invention it has been shown that biologically active cytokines or chemokines or derivatives or fragments thereof can be stably and efficiently expressed using an open reading frame different from the ORF expressing the NS1 protein. Alternatively additional leader sequences other than the natural signal peptides can be fused to the cytokines or chemokines which may further support efficient secretion of the protein and show a highly efficient induction of immune response in vivo.

Surprisingly, chemokines and cytokines can also be efficiently expressed when the amino acid sequence corresponding to the mature cytokine/chemokine is fused to a part of the NS1 protein via an amino acid sequence acting as a signal peptide. For example, this can be a part of the mouse IgKappa signal peptide.

According to the present invention the heterologous sequence preferably codes for interleukin 2 (IL-2) or a fragment or derivative thereof. IL-2 comprises secretory signal sequences and is an immunomodulatory, T-cell derived molecule required for the clonal expansion of antigen-activated T-cells. The secretion of IL-2 by CD4+ T lymphocytes has multiple biological effects, such as the induction of proliferation of T-helper and T-killer cells and the stimulation of T-cells to produce other cytokines. Furthermore, IL-2 can also activate B-cells, NK cells and macrophages. When IL-2 is expressed from recombinant viruses infecting non-lymphoid cells, its secretion could significantly decrease the pathogenesis of viral infection and modify the immune response. It is also known that IL-2 acts as immune adjuvant.

According to the present invention any fragment or derivative of the cytokines and chemokines is included that is still biologically active, i.e. shows immunomodulatory activities.

Alternatively, the cytokines/chemokines can also be selected from the group consisting of IL-15, GM-CSF, CCL3 or CCL20 or derivatives or fragments thereof.

Alternatively, it can be also any epitope or immunomodulatory region derived from Mycobacterium tuberculosis, for example ESAT-6.

Alternatively the heterologous sequences can also comprise chimeric proteins being cytokines or chemokines or fragments or derivatives thereof fused to antigenic proteins or antigenic peptides. Fusion can be either directly or via peptide linker sequences having a length of at least 4 amino acids, preferably at least 5 amino acids. For example, the linker sequences according to the invention are GGGS or GGGGS.

Examples for IL-2 chimeric proteins are known in the art. Exemplarily, this could be IL-2-PE40 (wherein PE is Pseudomonas exotoxin A), DAB389-IL-2 (where DAB is diphtheria toxin) or IL-2 Bax (wherein Bax is a proapoptotic protein of human origin) (Aqeilan R. et al., Biochem. J., 2003, 129-140).

According to the present invention the nucleotide sequences of the heterologous sequences which are introduced into the replication deficient influenza vector show at least 80% identity with their native sequences, preferably at least 85% identity, more preferred at least 90% identity. Any optimization of the nucleotide sequence in view of codon usage is included thereby.

Alternatively, the heterologous sequence can comprise B-cell or T-cell-epitopes, for example a B cell epitope from influenza hemagglutinin (HATB), for example the A loop epitope from the influenza virus hemagglutinin (HA) or parts thereof, or peptides representing one of the immunodominant epitopes of HA corresponding to amino acid sequence 150 to 159 (Caton et al., 1982, Cell, 417-427).

The epitope can also be derived from melanoma-associated endogenous retrovirus (MERV) as described in WO06/119527. It can be an epitope derived from the gag, pol or env protein of the virus, preferably from env. Especially, it can be one or more of the following peptides: EMQRKAPPRRRRHRNRA (SEQ ID. No 12); RMKLPSTKKAEPPTWAQ (SEQ ID. No 13); TKKAEPPTWAQLKKLTQ (SEQ ID. No 14); MPAGAAAANYTYWAYVP (SEQ ID. No 15); PIDDRCPAKPEEEGMMI (SEQ ID. No 16); YPPICLGRAPGCLMPAV (SEQ ID. No 17); YQRSLKFRPKGKPCPKE (SEQ ID. No 18); FRPKGKPCPKEIPKESK (SEQ ID. No 19); GKPCPKEIPKESKNTEV (SEQ ID. No 20); GTIIDWAPRGQFYHNCS (SEQ ID. No 21); RGQFYHNCSGQTQSCPS (SEQ ID. No 22); DLTESLDKHKHKKLQSF (SEQ ID. No 23); PWGWGEKGISTPRPKIV (SEQ ID. No 24); PKIVSPVSGPEHPELWR(SEQ ID. No 25); PRVNYLQDFSQRSLKF (SEQ ID. No 26); RVNYLQDFSYQRSLKFR(SEQ ID. No 27); VNYLQDFSYQRSLKFRP (SEQ ID. No 28); VNYLQDFSYQRSLKFRSP (SEQ ID. No 29); NYLQDFSYQRSLKFRPK (SEQ ID. No 30); YLQDFSYQRSLKFRPKG (SEQ ID. No 31); LQDFSYQRSLKFRPKGK (SEQ ID. No 32); QDFSYQRSLKFRPKGKP (SEQ ID. No 33); DFSYQRSLKFRPKGKPC (SEQ ID. No 34); FSYQRSLKFRPKGKPCP (SEQ ID. No 35); SYQRSLKFRPKGKPCPK (SEQ ID. No 36); YQRSLKFRPKGKPCPKE (SEQ ID. No 37); QRSLKFRPKGKPCPKEI (SEQ ID. No 38); RSLKFRPKGKPCPKEIP (SEQ ID. No 39); SLKFRPKGKPCPKEIPK (SEQ ID. No 40); LKFRPKGKPCPKEIPKE (SEQ ID. No 41); KFRPKGKPCPKEIPKES (SEQ ID. No 42); FRPKGKPCPKEIPKESK (SEQ ID. No 43); RPKGKPCPKEIPKESKN (SEQ ID. No 44); PKGKPCPKEIPKESKNT (SEQ ID. No 45); KGKPCPKEIPKESKNTE (SEQ ID. No 46); GKPCPKEIPKESKNTEV (SEQ ID. No 47); KPCPKEIPKESKNTEVL (SEQ ID. No 48); PCPKEIPKESKNTEVLV (SEQ ID. No 49); CPKEIPKESKNTEVLVW (SEQ ID. No 50); PKEIPKESKNTEVLVWE (SEQ ID. No 51); SYQRSLKFRPKGKPCPKEIP (SEQ ID. No 52).

According to an alternative embodiment of the invention the heterologous sequence is expressed from an open reading frame (ORF) different from the NS1 ORF. Another method for generating a second ORF can be achieved by incorporation of an internal ribosome entry site element (Garcia-Sastre A., et al., 1999, J. Virol., 75, 9029-9036) or doubling of influenza virus promoter sequences (Machado A. et al., 2003, Virology, 313, 235-249).

According to the present invention it has been surprisingly shown that even if the first approx. 12 amino acids of the NS1 protein are still present, secretion of the heterologous sequence is not prohibited Therefore, according to the present invention, the virus vector can contain at least 10 amino acids, preferably up to 30, preferably up to 20, preferred up to 14 amino acids of the N-terminus of the NS1 protein and a signal peptide or part thereof fused to the NS1 C-terminus. The C-terminal signal sequence is preferably present in case the NS1 protein contains not more than 30 amino acids of the N-terminus.

By using this specific construct, i.e. the fusion of a signal peptide or part thereof with said N-terminal amino acids of the NS1 protein, the so derived NS1 protein can be functionally modified to act as a signal peptide. Expression of heterologous sequences by said fusion peptides can increase the secretory characteristics of said heterologous sequences.

According to a preferred embodiment of the invention the translation of the NS1 protein is terminated by at least one stop codon and expression of said heterologous sequence is reinitiated by a start codon. For example, a stop-start cassette having the sequence UAAUG (SEQ ID. No 53) can be inserted into the influenza A virus NS gene coding sequence followed by the insertion of the heterologous sequence. In view of the short Stop-Start codon sequence and the limited capacity of the virus to express long sequence inserts when fused directly to or posttranslationally cleaved from NS1, the stop-start system can be highly advantageous compared to the incorporation of long sequences, i.e. of an internal ribosome entry site element. The stop-start codon can be inserted at any position within the NS gene between the splice donor and the splice acceptor site without modifying the nucleotide sequences of the functional splice sites.

In an alternative embodiment the stop-start codon is inserted at a position wherein at least 4 nucleotides, more preferred at least 6 nucleotides, (more preferred at least 8 nucleotides downstream) of the 5"splice donor site of the NS gene are expressed. The NS 5' and 3' intron boundaries are defined as the cleavage site between the first exon and the intron and the cleavage site between the intron and the second exon. In case of influenza A, the insertion of the start-stop codon is placed at any position within the NS gene, although at least 10 N-terminal amino acids of the NS1 protein, alternatively at least 12 N-terminal amino acids of the NS1 protein are expressed. Alternatively, the heterologous open reading frame can also be at least partially overlapping with the NS1 open reading frame.

In an embodiment of the invention the translation of the heterologous open reading frame is initiated from an optimized translation initiation sequence, preferably the translation initiation sequence is a Kozak consensus sequence (Kozak M., Nucleic Acids Research, 1984, 12, 857-872). This consensus sequence can comprise at least part of the sequence CCRGCCAUGG, wherein R can be A or G (SEQ ID NO. 54). Positions −3 (i.e., 3 nucleotides upstream from the ATG codon) and +4 have the strongest influence on translation (Kozak M., Nucleic Acids Research, 1987, 15, 8125-8148). Thus, the consensus sequence can also be RXXAUGG, XXAUGG or RXXAUG.

Furthermore according to the invention the NS gene segment contains a functional splice donor and/or acceptor splice site. According to the invention the splice donor and acceptor sites of the NS gene are consisting of the two nucleotides 3' to the 5' intron boundary and the two nucleotides 5' to the 3'intron boundary.

Homology to U1 snRNA or pyrimidine stretch can also be tested and developed to improve functional splice sites.

According to a specific embodiment, the NS gene segment contains a functional natural splice donor and acceptor splice site, i.e. the splice donor and acceptor sites are kept as natural sites, i.e. the nucleotides are not modified by artificial techniques.

Any nucleotide modifications at the splice sites occurring naturally due to modifications of influenza viruses based on environmental adaptations or natural strain developments are natural modifications and do not fall under the term synthetic or artificial modifications.

Alternatively, the sequences surrounding the splice donor and/or upstream of the acceptor site can be altered, Preferably, alteration or modification can be performed within 3 nucleotides 5' to the and/or 8 nucleotides 3' to the 5' border of the NS intron, as well as 100 nucleotides 5' to the and/or 2 nucleotides 3' to the 3' border of the NS intron. This is preferably by introducing synthetic sequences in order to modify splicing activity.

If e.g. insertion of a heterologous sequence increases NS intron size it may be preferable to modify the sequences surrounding the splice donor and/or acceptor site in order to increase splicing efficacy and thus genetic stability of the recombinant NS segment.

For example, it can be modified in that either the sequence surrounding the splice donor site is altered to increase the homology to the 5'end of the human U1 snRNA and/or the sequence upstream of the splice acceptor site containing the branch point (Plotch et al. 1986, Proc Natl Acad Sci USA. 83:5444-8; Nemeroff et al. 1992, Mol Cell Biol. 12:962-70) and the pyrimidine stretch is replaced by a sequence that enhances splicing of the NS segment.

For example, the sequence surrounding the 5' splice site can be changed from CAG/GTAGATTG (as found in the PR8 NS segment, (SEQ ID. No 55) to CAG/GTAAGTAT (nucleotides complementary to the 5' end of the human U1 snRNA are shown in bold italic letters, the splice donor site is indicated by "/", (SEQ ID. No 56).

In order to optimize splicing, the a preferred sequence introduced 5' of the splice acceptor site comprises a lariat consensus sequence and a pyrimidine stretch. For example, the sequence upstream of the synthetic splice acceptor site can be as follows:

TACTAACCTTCTTCTCTTTCTTCTCCTGACAG/ (SEQ ID. No 57)

The lariat consensus sequence is underlined, the pyrimidine stretch is bold, the 3' intron boundary is indicated by "/".

In view of stability of the virus vector and the expression rate of the heterologous sequence it can be important to introduce the synthetic/modified sequence containing a lariat consensus sequence and a pyrimidine stretch at a specific position within the NS gene, e.g. directly upstream of the slice acceptor site.

Furthermore, it may be necessary to vary the distance between the lariat consensus sequence and the pyrimidine stretch to modify the splicing rate of the NS segment (Plotch S. and Krug R., 1986, Proc. Natl. Acad. Sci., 83, 5444-5448; Nemeroff M. et al., 1992, Mol. Cell. Biol., 962-970).

In a preferred embodiment the replication deficient influenza virus according to the invention comprises a nucleotide sequence as shown in FIG. 1 (*a-j*) or is at least 96% homologous, alternatively at least 98% homologous.

In an additional embodiment, also a combination of at least two replication deficient influenza viruses according to the invention comprising at least one biologically active molecule or derivative or fragment thereof and at least one antigenic structure is claimed. Such combination comprising different heterologous sequences might be advantageous in view of further increasing humoral as well as cellular immunogenicity. For example, one of the vectors can contain a cytokine or fragment or derivative thereof like IL2 and a second virus vector can comprise an antigenic peptide or polypeptide.

Alternatively the heterologous sequences can also comprise fusion proteins wherein cytokines or chemokines or fragments or derivatives thereof are fused to antigenic proteins or antigenic peptides or linked directly or via a linker peptide to the NS1 protein derivative.

The present invention covers also a signal peptide comprising part of the N-terminal amino acids of an NS1 protein, for example 10-12 amino acids of the N-terminus of the NS1 protein, and a signal peptide or part thereof fused to the C-terminus of said NS1 peptide. Said signal peptide can consist of 8 to 30, preferably up to 50 amino acids.

The signal sequence can be derived from an antibody light chain, preferably from an Ig kappa chain, more preferably from mouse Ig kappa chain. According to an alternative embodiment, the Ig Kappa chain can comprise at least 10 amino acids, more preferred at least 12 amino acids, for example comprising the sequence METDTLLLWVLLLWVPGSTGD (SEQ ID. No. 11) or METDTLLLWVLLLWVPRSHG (SEQ ID No. 82) or part thereof.

A vaccine formulation comprising the replication deficient influenza virus vector according to the invention is also covered.

According to the invention the replication deficient influenza virus can be used for the preparation of a medicament for therapeutic treatment in patients, for example for the treatment of infectious diseases or cancer.

Methods of introduction include but are not limited to intradermal, intramuscular, intraperitoneal, intravenous, intranasal, epidural or oral routes. Introduction by intranasal routes is preferred.

In a preferred embodiment it may be desirable to introduce the medicament into the lungs by any suitable route. Pulmonary administration can also be employed, using e.g. an inhaler or nebulizer or formulate it with an aerosolizing agent.

The pharmaceutical preparation can also be delivered by a controlled release system, like a pump.

The medicament according to the invention can comprise a therapeutically effective amount of the replication deficient virus and a pharmaceutically acceptable carrier. "Pharmaceutically acceptable" means approved by regulatory authorities like FDA or EMEA. The term "carrier" refers to a diluent, adjuvant, excipient or vehicle with which the preparation is administered. Saline solutions, dextrose and glycerol solutions as liquid carriers or excipients like glucose, lactose, sucrose or any other excipients as known in the art to be useful for pharmaceutical preparations can be used. Additionally, also stabilizing agents can be included to increase shelf live of the medicament.

Preferably, a ready-to-use infusion solution is provided. Alternatively, the preparation can be formulated as powder which is solved in appropriate aqueous solutions immediately before application.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for administration are generally about $10^4$-$5 \times 10^7$ pfu and can be administered once, or multiple times with intervals as often as needed. Pharmaceutical compositions of the present invention comprising $10^4$-$5 \times 10^7$ pfu of mutant replication deficient viruses can be administered intranasally, intratracheally, intramuscularly or subcutaneously Effective doses may be extrapolated from dose-response curves derived from in vitro or animal model test systems.

Furthermore, a vector comprising a nucleotide sequence coding for a replication deficient influenza virus according to the invention is covered.

If a DNA vector is used, said vector is a transcription system for minus sense influenza RNA. For example it can be a vector as used by Hoffmann et al., 2000, Proc Natl Acad Sci USA. 97:6108-13. Alternatively, also an RNA comprising the sequence coding for the inventive replication deficient virus can be used.

Method for producing the inventive replication deficient influenza virus comprising the steps of: transfecting cells, preferably Vero cells, with at least one vector comprising the sequence for the inventive virus, incubating the transfected cells to allow for the development of viral progeny containing the heterologous protein is of course also covered by the invention.

Alternatively, a method for producing a replication deficient influenza virus is also provided, comprising the steps of: transforming a cell, preferably a Vero cell, with a vector comprising a nucleotide sequence coding for a replication deficient influenza virus according to the invention preferably together with a purified preparation of influenza virus RNP complex, infecting the selected cells with an influenza helper virus, incubating the infected cells to allow for the development of viral progeny and selecting transformed cells that express the modified NS gene and the heterologous sequence.

The foregoing description will be more fully understood with reference to the following examples. Such examples are, however, merely representative of methods of practicing one or more embodiments of the present invention and should not be read as limiting the scope of invention.

EXAMPLES

Example 1

Expression of Human Interleukin-2 from a Separate Open Reading Frame

A cDNA coding for human IL-2 was inserted into a modified NS segment of the influenza A strain Puerto Rico/8/34 that does not code for a functional NS1 protein. The NS1 protein was terminated after amino acid 21 by means of an artificially introduced Stop codon and thus does neither contain the RNA binding domain nor the effector domain.

To allow IL-2 translation the artificially introduced NS1 stop codon overlaps with the Start codon of IL-2 to give the sequence TAATG (SEQ ID No. 81). Two constructs were generated (see FIG. 2).

In both constructs (deINS1-IL-2-10 and deINS-IL-2-11) the IL-2 cDNA including the overlapping Stop/start codon replaces nucleotides 90-345 of the wild-type NS segment corresponding to amino acids 22-106 of the NS1 protein. Construct deINS-IL-2-10 thus comprises the natural splice acceptor site, the natural branch point 20 nucleotides upstream of the splice acceptor site (Plotch et al. 1986, Proc Natl Acad Sci USA. 83:5444-8; Nemeroff et al. 1992, Mol Cell Biol. 12:962-70) as well as the natural 11-nucleotide pyrimidine stretch of the wild-type NS segment. A lariat consensus sequence (CTRAY or YNYYRAY) that is found 72 nucleotdides upstream of the 3' splicing site in the wild-type NS segment is also present in the deINS-IL-2-10 segment.

In addition, in the deINS1-IL-2-11 segment a synthetic sequence of 29 nucleotides comprising a lariat consensus sequence followed by a 20-base pyrimidine stretch segment replaces nucleotides 361-525 of the wild-type NS segment corresponding to amino acids 112-166 of the NS1 protein. Thus also the natural branch point, the pyrimidine stretch as well as the lariat consensus sequence found 72 bases upstream of the 3' splicing site in the NS segment were replaced.

Furthermore, in both chimeric IL-2 NS segments the sequence downstream of the 5' intron boundary was changed to achieve 100% complementarity to the 5' end of the human U1 snRNA (i.e. /GTAGATTG as found in the wild type NS segment was changed to GTAAGTAT). In addition a methionine found in alternative reading frame at position 76 of the wild-type NS segment was changed to a valine. Thus the amino acid sequence of the truncated NS1 protein is MDPNTVSSFQVSIFLWRVRKR (letters shown underlined in bold denote changes from the wild-type NS sequence, (SEQ ID No. 59).

Description of the deINS1-IL-2-10 segment as shown in FIG. 1a: the ORF is consisting of the truncated NS1, i.e. the nucleotides 27-92; the human IL-2 ORF consists of nucleotides 92-553; The 5' intron boundary is located between nucleotides 56 and 57; the 3' intron boundary is between nucleotides 739 and 740 (SEQ ID No 1).

Description of the deINS1-IL-2-11 segment as shown in FIG. 1b: the ORF of the truncated NS1 consists of nucleotides 27-92; the human IL-2 ORF consists of nucleotides 92-553; the splice donor site is between nucleotides 56 and 57; the splice acceptor site is between nucleotides 603 and 604 (SEQ ID No 2);

Plasmid Constructions

As a backbone for construction of chimeric human Interleukin-2 NS segments the plasmid pKW2000 was used. pKW2000 was obtained by deleting the CMV promoter in pHW2000 (Hoffmann et al. 2000, Proc Natl Acad Sci USA. 97:6108-13). Thus upon transfection only vRNA is transcribed from pKW2000 derivatives.

DeINS1-IL-2-10 and deINS1-IL-2-11 segments were constructed by PCR standard methods and cloned into pKW2000 to yield the plasmids pKW-deINS-IL2-10 and pKW-deINS-IL-2-11, respectively. Analogously, a pKW2000 derivative containing the PR8 deINS segment (Garcia-Sastre et al. 1998, Virology. 252:324-30) was constructed (pKW-deINS1).

PA, PB1, PB2, HA, NA, M and NP segments derived from a Vero-cell adapted influenza A H1N1 virus strain (GHB01) were cloned into pHW2000.

All plasmids were sequenced to ensure the absence of unwanted mutations.

Generation of Viruses

Vero cells were maintained in DMEM/F12 medium containing 10% foetal calf serum and 1% Glutamax-I supplement at 37° C.

For virus generation seven pHW2000 derivatives containing the segments PA, PB1, PB2, HA, NA, M and NP derived from GHB01 as well as two protein expression plasmids coding for Influenza A PR8 NS1 (pCAGGS-NS1(SAM); (Salvatore et al. 2002, J. Virol. 76:1206-12)) and NEP (pcDNA-NEP) were used together with either pKW-deINS-IL-2-10, pKW-deINS-IL-2-11 or pKWdeINS1 for cotransfection of Vero cells. Following transfection, to support virus replication Vero cells were cultured in serum-free medium (Opti-Pro; Invitrogen) in the presence of 5 µg/ml trypsin. Three days after transfection 50-100% CPE was observed and rescued viruses were frozen or further amplified on Vero cells. In addition chimeric IL-2 expressing viruses were plaque purified once. After amplification on Vero cells several plaques were frozen for further analysis.

The generated viruses are designated GHB-IL-2-10, GHB-IL-2-11 and GHB01.

Analysis of Interleukin-2 Expression

Vero cells were infected at a multiplicity of infection of 0.1 with GHB-deINS1, GHB-IL-2-10 or GHB-IL-2-11 and incubated for 16 h at 37° C. in serum-free medium in the presence of 1 µg/ml trypsin. Subsequently, foetal calf serum (final concentration 10%) as well as soy bean trypsin inhibitor (final concentration 100 µg/ml) was added and incubation at 37° C. was continued for another 24 h.

Supernatants were analysed for secreted IL-2 by ELISA.

IL-2 expression was found to be about 5-fold higher for the GHB-IL-2-10 virus compared to the GHB-IL-2-11 virus (see FIG. 3). As expected, no IL-2 was detected in supernatants infected with GHB01 virus lacking the IL-2 cDNA.

The human-IL2 expression level in Vero cells was approx. 2600 pg/ml in GHB-IL-2-10 and approx. 500 pg/ml GHB-IL-2-11. In contrast, the expression level according to the state of the art was between 250-350 pg/ml (Kittel et al., 2005, s.above).

Analysis of Virus Stability

Chimeric IL-2 influenza viruses obtained either directly after transfection or after one round of plaque purification were serially passaged five times on Vero cells. RNA was extracted using a ViralAmp kit (Qiagen) and reverse transcribed. Whole NS segments were PCR amplified and subjected to agarose gel electrophoresis to evaluate the presence of deletions.

As shown in FIG. 4, deletion bands were found for all GHB-IL-2-10 virus samples regardless of plaque purification. In contrast, PCR products obtained for the GHB-IL-2-11 virus samples migrated at the expected size (see FIG. 4).

Example 2

Expression of Human Interleukin-2 from the NS1 Open Reading Frame

A cDNA coding for human IL-2 was inserted into a modified NS segment of the influenza A strain Puerto Rico/8/34 that does not code for a functional NS1 protein. In contrast to example 1, the IL-2 cDNA was directly fused to a truncated (12 amino acid) NS1 protein. Thus, IL-2 is expressed from the NS1 open reading frame (see FIG. 1c, deINS1-IL-2-14)

To allow IL-2 secretion, a cDNA coding for the mature IL-2 was fused to the first 12 aa of the NS1 protein via a modified Ig kappa signal peptide resulting in the following amino acid sequence:
MDPNTVSSFQVS-LLLWVLLLWVPGSTG-APTSSSTKKTQLQLEHLLLDLQMILNGINNYKNPK LTRMLTFKFYMPKKATELKHLQ CLEEELKPLEEVLNLAQSKNFHLR-PRDLISNINVIVLELKGSETTFMCEYA-DETATIVEFL NRWITFCQSIISTLT
(SEQ ID No. 60).

The first 12 amino acids of the above sequence correspond to the truncated NS1 protein, the amino acids corresponding to the modified mouse Ig kappa signal peptide are depicted in italic bold letter, and the remaining amino acid sequence corresponds to the mature human IL-2.

Description of the deINS1-IL-2-14 segment: ORF of the NS1-IgKappa-IL-2 fusion: nucleotides 27-509; Splice donor site between nucleotides 56 and 57; Splice acceptor site between nucleotides 559 and 560 (FIG. 1c)

Virus generation and analysis of IL-2 expression was done as described in example 1. The generated viruses was designated GHB-IL-2-14.

IL-2 expression levels were found to be about 17-times higher than for GHB-IL-2-11 (see FIG. 5). Thus, high level IL-2 expression from the truncated NS1 open reading frame is feasible.

Example 3

Influence of the Sequence Surrounding the Splice Donor Site on IL-2 Expression

To analyse the influence of the sequence surrounding the splice donor site on IL-2 expression, deINS1-IL-2-11 and deINS1-IL-2-14 were further modified. DeINS1-IL-2-13 was constructed from deINS1-IL-2-11 by changing the 8 nucleotides downstream of the 5' intron boundary from /GTAAG-TAT to /GTAGATTG as found in the wild type PR8 NS segment (nucleotides complementary to the 5' end of the human U1 snRNA are shown in bold italic letters, the 5' intron boundary is indicated by "/"). The deINS1-IL2-13 sequence is shown in FIG. 1d. Similarly, deINS1-IL-2-21 was constructed from deINS1-IL-2-14 by changing the sequence/ GTAAGTCT to /GTATTTGC (nucleotides complementary to the 5' end of the human U1 snRNA are shown in bold italic letters, the 5' intron boundary is indicated by "/").

The deINS1-IL2-21 sequence is shown in FIG. 1e.

Thus, in both constructs homology to the 5' end of the U1 snRNA was decreased when compared to their progenitor constructs.

For deINS1-IL-2-13 the amino acid sequence for the truncated NS1 protein is: MDPNTVSSFQVDCFLWRVRKR (SEQ ID NO. 61)

For deINS1-IL-2-21 the amino acid sequence for the NS1-IgK signal peptide-IL-2 fusion protein is: MDPNTVSSFQV-FALLWVLLLWVPGSTG-APTSSSTKKTQLQLE-HLLLDLQMILNGINNYKNPKLTRMLTFKFYMPK KATELKHLQC LEEELKPLEEVLNLAQSKNFHLR-PRDLISNINVIVLELKGSETTFMCEYADETATIVEF LNRWITFCQSIISTLT (SEQ ID NO. 62)

The first 11 amino acids of the above sequence correspond to the truncated NS1 protein, the amino acids corresponding to the modified mouse Ig kappa signal peptide are depicted in italic bold letter, and the remaining amino acid sequence corresponds to the mature human IL-2.

Viruses were generated and analysed for IL-2 expression as described in example 1. The generated viruses were designated GHB-IL-2-13 and GHB-IL-2-21. Genetic stability of the deINS1-IL-2-13 and deINS1-Il-2-21 segment was analysed after 5 consecutive passages on Vero cells as described in example 1.

IL-2 expression levels were found to be higher for the respective constructs that have a lower homology to the U1 sRNA around their splice donor site (see FIG. 5). Levels for GHB-IL-2-13 were found to be about 13-times higher than for the corresponding virus that exhibits a high homology to the U1 snRNA (GHB-IL-2-13; 9.4 ng/ml versus 0.7 ng/ml; FIG. 5). Similarly, IL-2 levels for GHB-IL-2-21 were found to be roughly 2.6-times higher than for GHB-IL-2-14 (31.1 ng/ml versus 12.1 ng/ml; FIG. 5).

Thus, by modifying the sequence around the NS splice donor site IL-2 expression levels can be tuned.

For both viruses, deINS1-IL-2-13 and deINS1-Il-2-21 no deletion bands were found after 5 consecutive passages indicating genetic stability.

Example 4

Expression of IL-2 from a Separate Open Reading Frame: Translation Initiation Via a Kozak Consensus Sequence The stop/start codon sequence in deINS1-IL-2-11 was replaced by a Kozak consensus sequence (i.e. the TAATG was replaced with TAAGCCGCCACCATG; the stop and start codon are indicated in bold underlined letters, SEQ ID No. 63) to yield the segment deINS1-IL-2-17.

The deINS1-IL-2-17 nucleotide sequence is shown in FIG. 1*f*.

Virus generation and analysis of IL-2 expression for GHB-IL-2-17 was performed as described in example 1. IL-2 expression levels were found to be about twice as high as for GHB-IL-2-11 (data not shown).

Example 5

Expression of Human IL-15 from the NS1 Open Reading Frame

A cDNA coding for human IL-15 is inserted into a modified NS segment of the influenza A strain Puerto Rico/8/34 that does not code for a functional NS1 protein. To allow secretion, the a cDNA encoding mature IL-15 is fused to a truncated (11 amino acid) NS1 ORF via a modified mouse Ig kappa signal peptide resulting in the following amino acid sequence: MDPNTVSSFQV-FALL WVLLLWVPRSHG-NWVNVISDLKKIEDLIQSMHIDAT-LYTESDVHPSCKVTAMKCFLLELQVISLESGDASI HDTVENLIILANNSLSSNGNVTESGCK-ECEELEEKNIKEFLQSFVHIVQMFINTS (SEQ ID No. 69).

The first 11 amino acids of the above sequence correspond to the truncated NS1 protein, the amino acids corresponding to the modified mouse Ig kappa signal peptide are depicted in italic bold letter, and the remaining amino acid sequence corresponds to the mature human IL-15.

The resulting chimeric IL-15 NS segment is referred to as deINS1-IL-15-21. The deINS1-IL-15-21 nucleotide sequence is shown in FIG. 1*g*

Virus generation is performed as described in example 1.

IL-15 expression levels in the supernatants of infected Vero cells were assessed by ELISA and were found to be in the range of 1-2 ng/ml.

Example 6

Expression of Human GM-CSF from the NS1 Open Reading Frame

A cDNA coding for human GM-CSF is inserted into a modified NS segment of the influenza A strain Puerto Rico/8/34 that does not code for a functional NS1 protein. To allow secretion, the mature GM-CSF cDNA is fused to a truncated (11 amino acid) NS1 protein via a modified mouse Ig kappa signal peptide resulting in the following amino acid sequence: MDPNTVSSFQV-FALLWVLLLWVPRSHG-APARSPSP-STQPWEHVNAIQEARRLLNLSRDTAAEM-NETVEVISEMFDLQEPTCLQ TRLELYKQGLRGSLT-KLKGPLTMMASHYKQHCP PTPETSCATQIITFESFKENLKDF LLVIPFDCWEPVQE (SEQ ID NO. 64)

The first 11 amino acids of the above sequence correspond to the truncated NS1 protein, the amino acids corresponding to the modified mouse Ig kappa signal peptide are depicted in italic bold letter, and the remaining amino acid sequence corresponds to the mature human GM-CSF.

The resulting chimeric GM-CSF NS segment is referred to as deINS1-GM-CSF-21.

The deINS1-GM-CSF-21 nucleotide sequence is shown in FIG. 1*h*

Virus generation is performed as described in example 1.

Example 7

Expression of Human CCL-3 from the NS1 Open Reading Frame

A cDNA coding for human CCL-3 (MIP-1alpha) is inserted into a modified NS segment of the influenza A strain Puerto Rico/8/34 that does not code for a functional NS1 protein.

To allow secretion, the mature CCL-3 cDNA is fused to a truncated (11 amino acid) NS1 protein via a modified mouse Ig kappa signal peptide resulting in the following amino acid sequence: MDPNTVSSFQV-FALLWVLLLWVPRSHG-APLAADTPTACCFSYTSRQIPQNFIADY-FETSSQCSKPSVIFLTKRGRQVCADPSEE WVQKYVS-DLELSA (SEQ ID NO. 65)

The first 11 amino acids of the above sequence correspond to the truncated NS1 protein, the amino acids corresponding to the modified mouse Ig kappa signal peptide are depicted in italic bold letter, and the remaining amino acid sequence corresponds to the mature human CCL-3.

The resulting chimeric CCL-3 NS segment is referred to as deINS1-CCL-3-21. The deINS1-CCL-3-21 nucleotide sequence is shown in FIG. 1*i*

Virus generation is performed as described in example 1.

Example 8

Expression of Human CCL-20 from the NS1 Open Reading Frame

A cDNA coding for human CCL-20 (MIP-3alpha) was inserted into a modified NS segment of the influenza A strain Puerto Rico/8/34 that does not code for a functional NS1 protein.

To allow secretion, the mature CCL-20 cDNA was fused to a truncated (11 amino acid) NS1 protein via a modified mouse Ig kappa signal peptide resulting in the following amino acid sequence: MDPNTVSSFQV-FALLWVLLLWVPRSHG- ASNFDCCLGYTDRILHPKFIVG-
FTRQLANEGCDINAIIFHTKKKLSVCANPKQTWVKYI
VRLLSKKVKNM (SEQ ID NO. 66)

The first 11 amino acids of the above sequence correspond to the truncated NS1 protein, the amino acids corresponding to the modified mouse Ig kappa signal peptide are depicted in italic bold letter, and the remaining amino acid sequence corresponds to the mature human CCL-20.

The resulting chimeric CCL-20 NS segment is referred to as deINS1-CCL-20-21.

The deINS1-CCL-20-21 nucleotide sequence is shown in FIG. 1j

Virus generation is performed as described in example 1.

CCL-20 expression levels in the supernatants of infected Vero cells were assessed by ELISA was found to be in the range of 25 ng/ml.

Example 9

Expression of Secreted Mycobacterium Tuberculosis ESAT-6 from the NS1 Open Reading Frame A cDNA coding for mycobacterium tuberculosis ESAT-6 was inserted into a modified NS segment of the influenza A strain Puerto Rico/8/34 that does not code for a functional NS1 protein.

To allow secretion, an ESAT-6 cDNA was fused to a truncated (11 amino acid) NS1 protein via a modified mouse Ig kappa signal peptide resulting in the following amino acid sequence: MDPNTVSSFQV-FALLWVLLLWVPRSHG-MTEQQWNFAGIEAAASAIQGNVTSIH-SLLDEGKQSLTKLAAAWGGSGSEAYQGVQ QKW-DATATELNNALQNLARTISEAGQAMASTEGNVTGMFA (SEQ ID NO. 70)

The first 11 amino acids of the above sequence correspond to the truncated NS1 protein, the amino acids corresponding to the modified mouse Ig kappa signal peptide are depicted in italic bold letter, and the remaining amino acid sequence corresponds to ESAT-6.

The resulting chimeric ESAT-6 NS segment is referred to as deINS1-ESAT-6s-21.

The deINS1-ESAT-6s-21 nucleotide sequence is shown in FIG. 1k

Virus generation was performed as described in example 1.

Example 10

Intracellular Expression of Mycobacterium Tuberculosis ESAT-6 from the NS1 Open Reading Frame A cDNA coding for mycobacterium tuberculosis ESAT-6 was inserted into a modified NS segment of the influenza A strain Puerto Rico/8/34 that does not code for a functional NS1 protein.

In contrast to example 9 an ESAT-6 cDNA was directly fused (i.e. without an amino acid sequence acting as a signal peptide) to a truncated (11 amino acid) NS1 protein resulting in the following amino acid sequence: MDPNTVSSFQV-FAMTEQQWNFAGIEAAASAIQGNVTSIH-SLLDEGKQSLTKLAAA WGGSGSEAYQGVQQKW-DATATELNNALQNLARTISEAGQAMASTEGNVTGMFA (SEQ ID NO. 71)

The first 11 amino acids of the above sequence correspond to the truncated NS1 protein, while the amino acid sequence shown in italic bold letters corresponds to ESAT-6.

The resulting chimeric ESAT-6 NS segment is referred to as deINS1-ESAT-6i-21.

The deINS1-ESAT-6i-21 nucleotide sequence is shown in FIG. 1l.

Virus generation was performed as described in example 1.

Example 11

Expression of IL-2 from the NS1 Open Reading Frame Using Alternative Signal Peptide Sequences The deINS1-IL2-21 segment (example 3) was modified by replacing the partial mouse IgK signal peptide sequence with other sequences. For deINS1-IL2-23 the amino acid sequence LLWVLLLWVPGSTG (SEQ ID No. 58) in deINS1-IL2-21 was replaced by the sequence WVLFILLLFLFLPRSHG (SEQ ID No. 72) resulting in the amino acid sequence MDP-NTVSSFQVFAWVLFILLLFLFLPRSHG-APTSSSTKK-TQLQLEHLLLDLQMILNGINNYKNPKL-TRMLTFKFYMPKKATELKHLQC
LEEELKPLEEVLNLAQSKNFHLR-
PRDLISNINVIVLELKGSETTFMCEYADETATIVEF LNRWITFCQSIISTLT (SEQ ID No. 73).

The deINS1-IL2-23 nucleotide sequence is shown in FIG. 1m.

For deINS1-IL2-24 the amino acid sequence LLWVLLL-WVPGSTG (SEQ ID No. 58) in deINS1-IL2-21 was replaced by the sequence AGAALLALLAALLPASRA (SEQ ID No. 74) which is derived from the human epidermal growth factor (hEGF) signal peptide (MRPSGTAGAALLALLAAL-CPASRA, (SEQ ID No. 75)) resulting in the amino acid sequence MDPNTVSSFQVFAAGAALLALLAALL-PASRAAPTSSSTKKTQLQLEHLLLDLQMILN GIN-NYKNPKLTRMLTFKFYMP-
KKATELKHLQCLEEELKPLEEVLNLAQSKNFHLRPR DLISNINVIVLELKGSETTFMCEYADE-
TATIVEFLNRWITFCQSIISTLT (SEQ ID No. 76).

The deINS1-IL2-24 nucleotide sequence is shown in FIG. 1n.

Virus generation was performed as described in example 1.

IL-2 expression levels in the supernatants of infected Vero cells were assessed by ELISA.

Thus, the partial mouse IgK signal peptide can be replaced by other sequences acting as a signal peptide.

Example 12

Modification of Sequences Surrounding the Splice Donor and Acceptor Site Affects NS Splicing Efficiency To analyse the influence of the sequences surrounding the intron boundaries on splicing efficiency deINS1-IL-2-10 (see example 1) was further modified. DeINS1-IL-2-12 was constructed from deINS1-IL-2-10 by changing the 8 nucleotides downstream of the 5' intron boundary from /GTAAGTAT to /GTAGATTG as found in the wild type PR8 NS segment (nucleotides complementary to the 5' end of the human U1 snRNA are shown in bold italic letters, the splice donor site is indicated by "/"). Otherwise the deINS1-IL-2-12 nucleotide sequence is identical to deINS1-IL-2-10.

Virus generation was done as described in example 1.

Genetic stability of the deINS1-IL-2-12 segment was analysed after 5 consecutive passages as described in example 1. Clear deletion bands were found (data not shown).

To analyse splicing efficacy, Vero cells were cotransfected with four plasmids expressing PB1, PB2, PA and NP proteins along with a plasmid expressing vRNA of deINS1-IL-2-10, deINS1-IL-2-11 (see example 1), deINS1-IL-2-12 or deINS1-IL-2-13 (see example 3).

24 hours later mRNA was extracted from transfected cells and analysed for spliced and unspliced deINS1-IL-2 mRNA species by Real Time PCR.

The following table summarises the sequence modifications performed either 3' to the splice donor site or 5' to the splice acceptor site as well as genetic stability and IL-2 expression levels (IL-2 expression for deINS1-IL-2-10 and deLNS1-IL-2-12 are not given since both segments appeared genetically unstable).

| segment | delNS1-IL-2-12 | delNS1-IL-2-10 | delNS1-IL-2-13 | delNS1-IL-2-11 |
|---|---|---|---|---|
| Sequence 3' to splice donor site | wild-type | modified | wild-type | modified |
| Sequence 5' to 3' splice acceptor site | wild-type | wild-type | modified | modified |
| Genetic stability | negative | negative | positive | positive |
| IL-2 expression | na | na | 8 ng | 700 pg |

As shown in FIG. 7, deINS1-IL-2 mRNA splicing can be altered by either modifying the sequence surrounding the splice donor site or the sequences 5' to the splice acceptor site.

It is also apparent, that increasing splicing efficiency above a certain threshold necessary to achieve genetic stability reduces IL-2 expression (deINS1-IL-2-13 versus deINS1-IL-2-11).

Example 13

Expression of Human Interleukin-2 from a Separate Open Reading Frame of Influenza B A cDNA coding for human IL-2 was inserted into a modified NS segment of the influenza B strain B/Vienna/33/06. The NS1 protein was terminated after amino acid 38 by means of an artificially introduced Stop codon and thus does neither contain the RNA binding domain nor C-terminal domain of NS1.

To allow IL-2 translation the artificially introduced NS1 stop codon overlaps with the Start codon of IL-2 to give the sequence TAATG. A schematic expression scheme is given in FIG. 8. In this construct (ΔNS1-38IL2), the IL-2 cDNA including the overlapping Stop/start codon replaces nucleotides 159-728 of the wild-type NS segment corresponding to amino acids 38-228 of the NS1 protein.

In this construct, a synthetic sequence of 29 nucleotides comprising a lariat consensus sequence followed by a 20-base pyrimidine stretch segment replaces the natural splice acceptor site plus the natural pyrimidine stretch analogous to the influenza A construct deINS1-IL-2-11.

Description of the ΔNS1-38IL2 segment as shown in FIG. 8: the ORF of the truncated NS1 consists of nucleotides 45-158; the human IL-2 ORF consists of nucleotides 161-619; the 5' intron boundary is between nucleotides 77 and 78; the 3' intron boundary is between nucleotides 657 and 658.

Generation of Plasmids and Viruses

Plasmids for influenza B Viruses were generated analogous to the influenza A plasmids using standard cloning techniques. HA and NA derived from a Vero-cell adapted influenza B/Thüringen/2/06 strain and PA, PB1, PB2, M and NP segments derived from a Vero-cell adapted influenza B/Vienna/33/06 virus strain and were cloned into pHW2006. All plasmids were sequenced to ensure the absence of unwanted mutations.

The IL2 expressing influenza virus was generated as described for influenza A and designated ΔNS1-38IL2.

Analysis of Virus Stability

Chimeric IL-2 influenza viruses obtained directly after transfection were serially passaged four times on Vero cells. RNA was extracted using a ViralAmp kit (Qiagen) and reverse transcribed. Whole NS segments were PCR amplified and subjected to agarose gel electrophoresis to evaluate the presence of deletions. PCR products obtained for the ΔNS1-38IL2 virus samples after 1 and 4 passages migrated at the expected size, indicating that the IL2 expressing vector is stable.

Immunogenicity in Mice

To investigate the immunogenic potential, mice were immunized with $1*10^5$ TCID$_{50}$/mouse with wt influenza B Virus, ΔNS1-38IL2, ΔNS1-38 (a control Virus which was constructed similar to ΔNS1-38IL2 but without the insertion of IL2) or PBS as a control. Four weeks post immunization, mice were challenged with $2*10^5$ TCID$_{50}$/mouse of homologous influenza B wt virus. Three days post infection, mice were sacrificed and viral replication was investigated in lungs and nasal turbinates were. Mice which were immunized with the wt influenza Virus were protected in lungs and noses whereas in the control mice immunized with PBS, viral titres of approximately 3 logs in both, nasal and lung tissues. At the dose of $1*10^5$ TCID$_{50}$/mouse none of the mice immunized with ΔNS1-38 was protected from wt influenza challenge manifesting nasal and lung tissues comparable to the naïve animals. In contrast, no virus could be isolated from any mouse immunized with virus ΔNS1-38IL2 at the same dose, indicating that all mice were protected.

What is claimed is:

1. A replication deficient influenza virus, characterized in that the virus comprises:
   a) a modified NS segment coding for a NS1 protein comprising at least one amino acid modification within positions 1 to 73 resulting in a complete lack of functional RNA binding and at least one amino acid modification between position 74 and the carboxy-terminal amino acid residue resulting in a complete lack of effector function, and
   b) a heterologous sequence between a functional splice donor site and a functional splice acceptor site inserted in the NS gene segment,
   wherein the virus comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:67, SEQ ID NO:68, SEQ ID NO:78, and SEQ ID NO:79.

2. A replication deficient influenza virus according to claim 1, further comprising a signal peptide or part thereof fused to the C-terminus of NS1 protein.

3. A replication deficient influenza virus according to claim 1, wherein the virus further comprises a lariat consensus sequence upstream of the splice acceptor site.

4. A replication deficient influenza virus according to claim 1, wherein the virus is formulated as a vaccine.

5. A vector comprising a nucleotide sequence coding for a replication deficient influenza virus according to claim 1.

6. A replication deficient influenza virus according to claim 1, wherein the virus comprises SEQ ID NO:1.

7. A replication deficient influenza virus according to claim 1, wherein the virus comprises SEQ ID NO:2.

8. A replication deficient influenza virus according to claim 1, wherein the virus comprises SEQ ID NO:3.

9. A replication deficient influenza virus according to claim 1, wherein the virus comprises SEQ ID NO:4.

10. A replication deficient influenza virus according to claim 1, wherein the virus comprises SEQ ID NO:5.

11. A replication deficient influenza virus according to claim 1, wherein the virus comprises SEQ ID NO:6.

12. A replication deficient influenza virus according to claim 1, wherein the virus comprises SEQ ID NO:7.

13. A replication deficient influenza virus according to claim 1, wherein the virus comprises SEQ ID NO:8.

14. A replication deficient influenza virus according to claim 1, wherein the virus comprises SEQ ID NO:9.

15. A replication deficient influenza virus according to claim 1, wherein the virus comprises SEQ ID NO:10.

16. A replication deficient influenza virus according to claim 1, wherein the virus comprises SEQ ID NO:67.

17. A replication deficient influenza virus according to claim 1, wherein the virus comprises SEQ ID NO:68.

18. A replication deficient influenza virus according to claim 1, wherein the virus comprises SEQ ID NO:78.

19. A replication deficient influenza virus according to claim 1, wherein the virus comprises SEQ ID NO:79.

* * * * *